US011166731B2

(12) United States Patent
Wolfe et al.

(10) Patent No.: US 11,166,731 B2
(45) Date of Patent: Nov. 9, 2021

(54) SYSTEMS AND METHODS FOR TREATING ANEURYSMS

(71) Applicant: Galaxy Therapeutics, Inc., Milpitas, CA (US)

(72) Inventors: Thomas J. Wolfe, Shorewood, WI (US); Osama O. Zaidat, Lambertville, MI (US); Brett Follmer, Santa Clara, CA (US); Edgard Luiz Ramos Pereira, Boca Raton, FL (US); Arturo Rosqueta, San Jose, CA (US); Aamir Badruddin, Bolingbrook, IL (US)

(73) Assignee: Galaxy Therapeutics Inc., Milpitas, CA (US)

( * ) Notice: Subject to any disclaimer, the term of this patent is extended or adjusted under 35 U.S.C. 154(b) by 0 days.

(21) Appl. No.: 16/840,421

(22) Filed: Apr. 5, 2020

(65) Prior Publication Data

US 2020/0367897 A1 Nov. 26, 2020

Related U.S. Application Data

(60) Provisional application No. 62/852,988, filed on May 25, 2019, provisional application No. 62/914,442, (Continued)

(51) Int. Cl.
*A61B 17/12* (2006.01)
*A61B 17/00* (2006.01)
*A61B 90/00* (2016.01)

(52) U.S. Cl.
CPC .. *A61B 17/12113* (2013.01); *A61B 17/00234* (2013.01); *A61B 17/12031* (2013.01);
(Continued)

(58) Field of Classification Search
CPC ........ A61B 17/12113; A61B 17/00234; A61B 17/12172; A61B 17/12177;
(Continued)

(56) References Cited

U.S. PATENT DOCUMENTS 5,250,071 A 10/1993 Palermo
5,282,806 A 2/1994 Haber et al.
(Continued)

FOREIGN PATENT DOCUMENTS

CN 102871700 B 4/2015
CN 103006285 B 6/2015
(Continued)

OTHER PUBLICATIONS

Shapiro, M., Raz, E., Becske, T., Nelson, P., "Variable Porosity of the Pipeline Embolization Device in Straight and Curved Vessels: A Guide for Optimal Deployment Strategy", Original Research Interventional, Sep. 26, 2013, 6 pages, 10.3174/ajnr.A3742, American Society of Neuroradiology, Oak Brook, USA.
(Continued)

*Primary Examiner* — Erich G Herbermann
(74) *Attorney, Agent, or Firm* — Blair Walker IP Services, LLC

(57) ABSTRACT

An apparatus for treating an aneurysm includes an occlusion element configured to be releasably coupled to an elongate delivery shaft and including an inverted mesh tube having an outer layer and an inner layer, the outer layer transitioning to the inner layer at an inversion fold, the occlusion element configured to be delivered in a collapsed configuration through an inner lumen of a delivery catheter and further configured to expand to an expanded configuration when advanced out of the delivery catheter, wherein in the expanded configuration, at least the outer layer of the inverted mesh tube is formed into an expanded shape
(Continued)

including a proximal section having a first transverse dimension, a distal section having a second transverse dimension, and a waist portion having a third transverse dimension, wherein the third transverse dimension is less than the first transverse dimension, and the third transverse dimension is less than the second transverse dimension, and wherein in the expanded configuration, the waist portion is configured to be deformed by an externally applied force such that a distance between the distal section and the proximal section is decreased.

29 Claims, 14 Drawing Sheets

Related U.S. Application Data filed on Oct. 12, 2019, provisional application No. 62/975,741, filed on Feb. 12, 2020, provisional application No. 62/975,744, filed on Feb. 12, 2020.

(52) U.S. Cl.
CPC .. *A61B 17/12172* (2013.01); *A61B 17/12177* (2013.01); *A61B 2017/00867* (2013.01); *A61B 2017/1205* (2013.01); *A61B 2017/12054* (2013.01); *A61B 2017/12059* (2013.01); *A61B 2017/12063* (2013.01); *A61B 2017/12068* (2013.01); *A61B 2090/3966* (2016.02)

(58) Field of Classification Search
CPC .... A61B 2017/00867; A61B 17/12031; A61B 2090/3966; A61B 2017/1205; A61B 2017/12054; A61B 2017/12059; A61B 2017/12063; A61B 2017/12068
See application file for complete search history.

(56) References Cited

U.S. PATENT DOCUMENTS

| | | | |
|---|---|---|---|
| 5,304,195 A | 4/1994 | Twyford, Jr. et al. |
| 5,556,390 A | 9/1996 | Hicks |
| 5,795,331 A | 8/1998 | Cragg et al. |
| 5,935,148 A | 8/1999 | Villar |
| 6,086,577 A | 7/2000 | Ken et al. |
| 6,152,144 A | 11/2000 | Lesh et al. |
| 6,391,037 B1 | 5/2002 | Greenhalgh |
| 6,454,780 B1 | 9/2002 | Wallace |
| 6,506,204 B2 | 1/2003 | Mazzochi |
| 6,510,811 B1 | 1/2003 | Gore et al. |
| 6,544,163 B2 | 4/2003 | Wallace et al. |
| 6,613,074 B1 | 9/2003 | Mitelberg et al. |
| 6,936,055 B1 | 8/2005 | Ken et al. |
| 6,994,689 B1 | 2/2006 | Zadno-Azizi et al. |
| 7,128,736 B1 | 10/2006 | Abrams et al. |
| 7,195,636 B2 | 3/2007 | Avellanet et al. |
| 7,229,461 B2 | 6/2007 | Chin et al. |
| 7,367,985 B2 | 5/2008 | Mazzocchi et al. |
| 7,410,482 B2 | 8/2008 | Murphy et al. |
| 7,569,066 B2 | 8/2009 | Gerberding et al. |
| 7,749,242 B2 | 7/2010 | Tran et al. |
| 8,142,456 B2 | 3/2012 | Rosqueta et al. |
| 8,333,796 B2 | 12/2012 | Tompkins et al. |
| 8,388,650 B2 | 3/2013 | Gerberding et al. |
| 8,398,670 B2 | 3/2013 | Amplatz et al. |
| 8,551,132 B2 | 10/2013 | Eskridge et al. |
| 8,597,320 B2 | 12/2013 | Sepetka et al. |
| 8,728,117 B1 | 5/2014 | Janardhan et al. |
| 8,777,979 B2 | 7/2014 | Shrivastava et al. |
| 8,820,207 B2 | 9/2014 | Marchand et al. |
| 8,826,791 B2 | 9/2014 | Thompson et al. |
| 8,864,790 B2 | 10/2014 | Strauss et al. |
| 8,864,791 B2 | 10/2014 | Bloom et al. |
| 8,940,015 B2 | 1/2015 | Kariniemi |
| 8,998,947 B2 | 4/2015 | Aboytes et al. |
| 9,107,670 B2 | 8/2015 | Hannes et al. |
| 9,198,668 B2 | 12/2015 | Theobald et al. |
| 9,259,337 B2 | 2/2016 | Cox et al. |
| 9,314,326 B2 | 4/2016 | Wallace et al. |
| 9,585,670 B2 | 3/2017 | Hines |
| 9,597,087 B2 | 3/2017 | Marchand et al. |
| 9,636,117 B2 | 5/2017 | Bachman et al. |
| 9,669,188 B2 | 6/2017 | Echarri et al. |
| 9,855,052 B2 | 1/2018 | Aboytes et al. |
| 9,918,720 B2 | 3/2018 | Marchand et al. |
| 9,980,733 B2 | 5/2018 | Badruddin et al. |
| 10,111,670 B2 | 10/2018 | Lorenzo et al. |
| 10,136,896 B2 | 11/2018 | Hewitt et al. |
| 10,149,676 B2 | 12/2018 | Mirigian et al. |
| 10,478,195 B2 | 11/2019 | Aboytes et al. |
| 10,751,065 B2 | 8/2020 | Soto Del Valle et al. |
| 2002/0169473 A1 | 11/2002 | Sepetka et al. |
| 2002/0188314 A1 | 12/2002 | Anderson et al. |
| 2003/0171770 A1 | 9/2003 | Kusleika et al. |
| 2003/0176884 A1 | 9/2003 | Berrada et al. |
| 2003/0195553 A1 | 10/2003 | Wallace et al. |
| 2004/0034386 A1 | 2/2004 | Fulton et al. |
| 2004/0044391 A1 | 3/2004 | Porter |
| 2004/0172056 A1 | 9/2004 | Guterman et al. |
| 2004/0199201 A1 | 10/2004 | Kellett et al. |
| 2005/0033409 A1 | 2/2005 | Burke et al. |
| 2005/0107823 A1 | 5/2005 | Leone et al. |
| 2005/0171478 A1 | 8/2005 | Selmon et al. |
| 2005/0277978 A1 | 12/2005 | Greenhalgh |
| 2006/0064151 A1 | 3/2006 | Guterman et al. |
| 2006/0106417 A1 | 5/2006 | Tessmer et al. |
| 2006/0155323 A1 | 7/2006 | Porter et al. |
| 2007/0173928 A1 | 7/2007 | Morsi |
| 2007/0208376 A1 | 9/2007 | Meng |
| 2007/0225794 A1 | 9/2007 | Thramann et al. |
| 2007/0270902 A1 | 11/2007 | Slazas et al. |
| 2008/0045997 A1 | 2/2008 | Balgobin et al. |
| 2008/0097495 A1 | 4/2008 | Feller, III et al. |
| 2008/0147100 A1 | 6/2008 | Wallace |
| 2008/0281350 A1 | 11/2008 | Sepetka et al. |
| 2008/0319533 A1 | 12/2008 | Lehe |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0177261 A1 | 7/2009 | Teoh et al. |
| 2009/0264978 A1 | 10/2009 | Dieck et al. |
| 2009/0287291 A1 | 11/2009 | Becking et al. |
| 2009/0318941 A1 | 12/2009 | Sepetka et al. |
| 2010/0179583 A1 | 7/2010 | Carpenter et al. |
| 2011/0046719 A1 | 2/2011 | Frid |
| 2011/0202085 A1 | 8/2011 | Loganathan et al. |
| 2012/0065667 A1 | 3/2012 | Javois et al. |
| 2012/0071911 A1 | 3/2012 | Sadasivan et al. |
| 2012/0143317 A1 | 6/2012 | Cam et al. |
| 2012/0259244 A1 | 10/2012 | Roberts et al. |
| 2012/0283768 A1 | 11/2012 | Cox et al. |
| 2012/0303052 A1 | 11/2012 | Connor |
| 2012/0310270 A1 | 12/2012 | Murphy et al. |
| 2012/0330347 A1 | 12/2012 | Becking et al. |
| 2013/0066357 A1 | 3/2013 | Abotes et al. |
| 2013/0073026 A1 | 3/2013 | Russo et al. |
| 2013/0190800 A1 | 7/2013 | Murphy et al. |
| 2013/0211495 A1 | 8/2013 | Halden et al. |
| 2014/0005714 A1 | 1/2014 | Quick et al. |
| 2014/0012303 A1 | 1/2014 | Heipl |
| 2014/0052233 A1 | 2/2014 | Cox et al. |
| 2014/0172001 A1 | 6/2014 | Becking et al. |
| 2014/0257360 A1 | 9/2014 | Keillor |
| 2014/0343602 A1 | 11/2014 | Cox et al. |
| 2015/0005811 A1 | 1/2015 | Lubock et al. |
| 2015/0133989 A1 | 5/2015 | Lubock et al. |
| 2015/0250628 A1 | 9/2015 | Monstadt et al. |
| 2015/0272589 A1 | 10/2015 | Lorenzo |
| 2015/0313605 A1 | 11/2015 | Griffin |
| 2016/0022445 A1 | 1/2016 | Ruvalcava et al. |
| 2016/0030050 A1 | 2/2016 | Franano et al. |
| 2016/0278749 A1 | 9/2016 | Javois et al. |

(56) References Cited

U.S. PATENT DOCUMENTS

| | | |
|---|---|---|
| 2016/0317277 A1 | 11/2016 | Carpenter et al. |
| 2017/0014114 A1 | 1/2017 | Radfiee et al. |
| 2017/0156734 A1 | 6/2017 | Griffin |
| 2017/0224350 A1 | 8/2017 | Shimizu et al. |
| 2017/0224355 A1 | 8/2017 | Bowman et al. |
| 2017/0348014 A1 | 12/2017 | Wallace et al. |
| 2017/0367708 A1 | 12/2017 | Mayer et al. |
| 2017/0367713 A1 | 12/2017 | Greene, Jr. et al. |
| 2018/0049731 A1 | 2/2018 | Hardy et al. |
| 2019/0053810 A1 | 2/2019 | Griffin |
| 2019/0110796 A1* | 4/2019 | Jayaraman ......... A61B 17/0057 |
| 2019/0192165 A1 | 6/2019 | Greene, Jr. et al. |
| 2019/0192167 A1 | 6/2019 | Lorenzo |
| 2019/0192168 A1 | 6/2019 | Lorenzo |
| 2019/0223876 A1 | 7/2019 | Badruddin et al. |
| 2019/0223878 A1* | 7/2019 | Lorenzo ........... A61B 17/12031 |
| 2019/0223881 A1 | 7/2019 | Hewitt et al. |
| 2019/0357914 A1 | 11/2019 | Gorochow et al. |
| 2020/0113576 A1 | 4/2020 | Gorochow et al. |

FOREIGN PATENT DOCUMENTS

| | | |
|---|---|---|
| DE | 102012016555 A1 | 2/2014 |
| DE | 102013006503 A1 | 7/2014 |
| EP | 0832607 A1 | 4/1998 |
| EP | 2647343 B1 | 7/2017 |
| WO | WO1999/05977 A1 | 2/1999 |
| WO | WO2002/00139 A1 | 1/2002 |
| WO | WO2009/132045 A2 | 10/2009 |
| WO | WO2017/102804 A1 | 6/2017 |
| WO | WO2017/153603 A1 | 9/2017 |
| WO | WO2017/220400 A1 | 12/2017 |
| WO | WO2019038293 A1 | 2/2019 |

OTHER PUBLICATIONS

Perez, M., Henkes, H., Bouillot, P., Brina, O., Slater, L., Pereira, V., "Intra-aneurysmal hemodynamics: evaluation of pCONus and pCANvas bifurcation aneurysm devices using DSA optical flow imaging", Journal of NeuroInterventional Surgery, Dec. 23, 2015, 6 pages, 10.1136/neurintsurg-2015-011927, Society of NeuroInterventional Surgery, Fairfax, USA.

Torii, R., Oshima, M., Kobayashi, T., Takagi, K., Tezduyar, T., "Fluid-structure interaction modeling of a patient-specific cerebral aneurysm: influence of structural modeling." Computational Mechanics 43: 151-159 (2008).

Control, etc. http://www.asianjns.org/articles/2012/7/4/images/AsianJNeurosurg_2012_7_4_159_106643_f7.jpg downloaded from internet Apr. 3, 2020.

Cerus https://neuronewsinternational-wpengine.netdna-ssl.com/wp-content/uploads/sites/3/2016/07/Cerus-Endovascular-Contour-300x194.jpg downloaded from internet Apr. 3, 2020.

Contour https://neuronewsinternational-wpengine.netdna-ssl.com/wp-content/uploads/sites/3/2017/06/Contour-e1497957260381-300x194.png downloaded from internet Apr. 3, 2020.

Medtronic https://evtoday.com/images/articles/2017-02/0217-endovascular-fig1.png downloaded from internet Apr. 3, 2020.

Bhogal, P., Udani, S., Cognard, C., Piotin, M., Brouwer, P., Sourour, N., Andersson, T., Makalanda, L., Wong, K., Fiorella, D., Arthur, A., Yeo, L., Soderman, M., Henkes, H., Pierot, L., "Endovascular flow disruption: where are we now?" Journal of NeuroInterventional Surgery 11: 1024-1035 (2019).

* cited by examiner

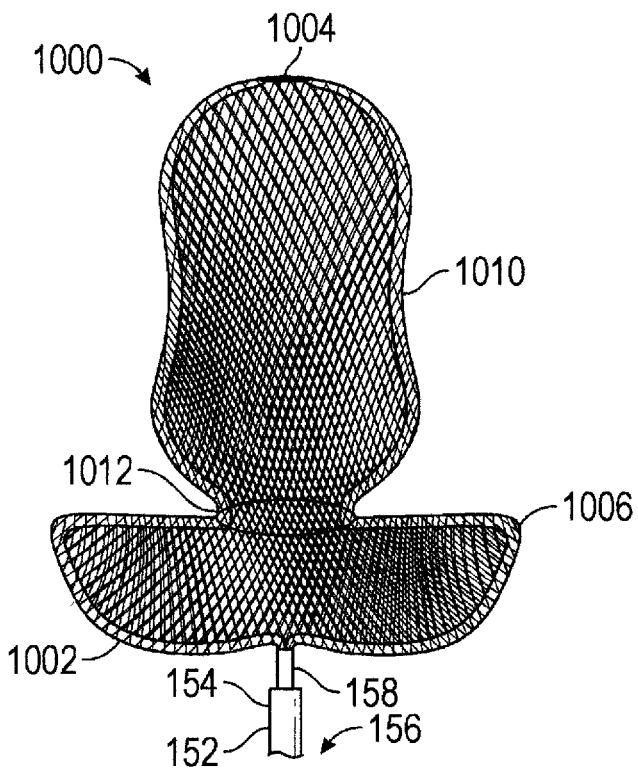
FIG. 25
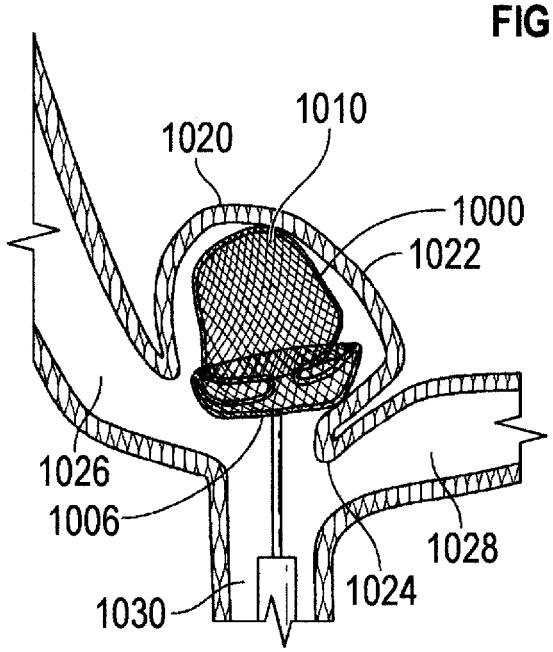 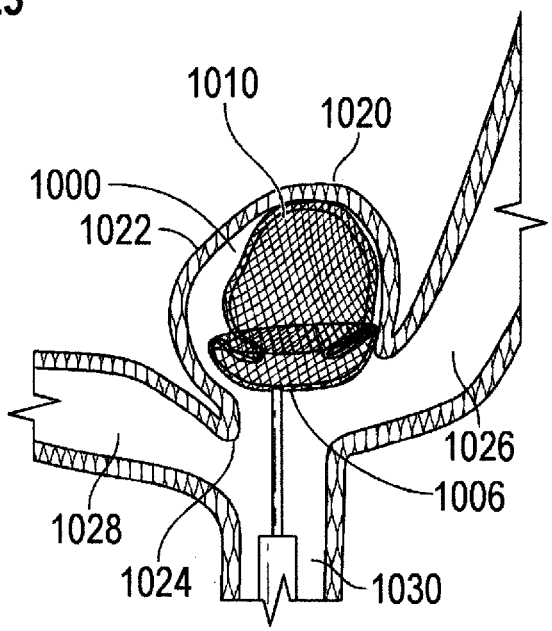
FIG. 26 FIG. 27

SYSTEMS AND METHODS FOR TREATING ANEURYSMS

INCORPORATION BY REFERENCE TO ANY PRIORITY APPLICATIONS

This application claims the benefit of priority to U.S. Provisional Patent Application No. 62/852,988, filed on May 25, 2019, U.S. Provisional Patent Application No. 62/914,442, filed on Oct. 12, 2019, U.S. Provisional Patent Application No. 62/975,741, filed on Feb. 12, 2020, and U.S. Provisional Patent Application No. 62/975,744, filed on Feb. 12, 2020, all of which are herein incorporated by reference in their entirety for all purposes. Priority is claimed pursuant to 35 U.S.C. § 119.

BACKGROUND OF THE INVENTION

Field of the Invention

The field of the invention generally relates to embolic devices for filling spaces in the vascular system, including cerebral aneurysms or left atrial appendages. In some case, the embolic devices may be used to embolize native vessels.

Description of the Related Art

An embolic device may be used as a stand-alone device to occlude and aneurysm, or may be used with an adjunctive device or material.

SUMMARY OF THE INVENTION

In one embodiment of the present disclosure, an apparatus for treating an aneurysm in a blood vessel includes an occlusion element configured to be releasably coupled to an elongate delivery shaft, the occlusion element including a mesh body configured to be delivered in a collapsed configuration through an inner lumen of a delivery catheter, the inner lumen having a proximal end and a distal end, the body further configured to expand to an expanded configuration when advanced out of the distal end of the inner lumen of the delivery catheter and into the aneurysm, wherein the body includes a proximal portion having a proximal maximum transverse dimension A and a distal maximum transverse dimension B and a frustoconical portion extending between the proximal maximum transverse dimension A and the distal maximum transverse dimension B, and wherein the body further includes distal portion having a maximum transverse dimension C and a waist portion between the proximal portion and the distal portion, and wherein the dimension A is between about 50% and about 100% of dimension B.

In another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a waist portion having a third diameter, wherein the third diameter is less than the first diameter and the third diameter is less than the second diameter.

In yet another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, wherein at least the outer layer is formed into an expanded shape having a proximal section having a first diameter, a distal section having a second diameter, and a first waist portion having a third diameter, a middle section having a fourth diameter, and a second waist portion having a fifth diameter, wherein the first diameter, the second diameter, and the fourth diameter are each greater than the third diameter, and wherein the first diameter, the second diameter, and the fourth diameter are each greater than the fifth diameter.

In still another embodiment of the present disclosure, a method for forming an apparatus for treating an aneurysm in a blood vessel includes forming a mesh tube, inverting the mesh tube to form an outer layer and an inner layer, the outer layer transitioning to the inner layer at an inversion fold, forming at least the outer layer into an expanded shape having a proximal section having a first diameter and a distal section having a second diameter, and etching the distal section to decrease its stiffness.

In yet another embodiment of the present disclosure, an apparatus for treating an aneurysm in a blood vessel includes an occlusion element configured to be releasably coupled to an elongate delivery shaft, the occlusion element including an inverted mesh tube having an outer layer and an inner layer, the outer layer transitioning to the inner layer at an inversion fold, the occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter and into the aneurysm, wherein in the expanded configuration, at least the outer layer of the inverted mesh tube is formed into an expanded shape including a proximal section having a first transverse dimension, a distal section having a second transverse dimension, and a waist portion having a third transverse dimension, wherein the third transverse dimension is less than the first transverse dimension, and the third transverse dimension is less than the second transverse dimension, and wherein in the expanded configuration, the waist portion is configured to be deformed by an externally applied force such that a distance between the distal section and the proximal section is decreased.

BRIEF DESCRIPTION OF THE DRAWINGS

FIG. 25 is a plan view of the occlusion device of FIG. 24 releasably coupled to a pusher, according to an embodiment of the present disclosure.

FIG. 26 is a perspective view of the occlusion device of FIG. 24 implanted within a simulated aneurysm, according to an embodiment of the present disclosure.

FIG. 27 is a perspective view of the occlusion device of FIG. 24 implanted within a simulated aneurysm, according to an embodiment of the present disclosure.

DETAILED DESCRIPTION OF THE ILLUSTRATED EMBODIMENTS

Figure 1:
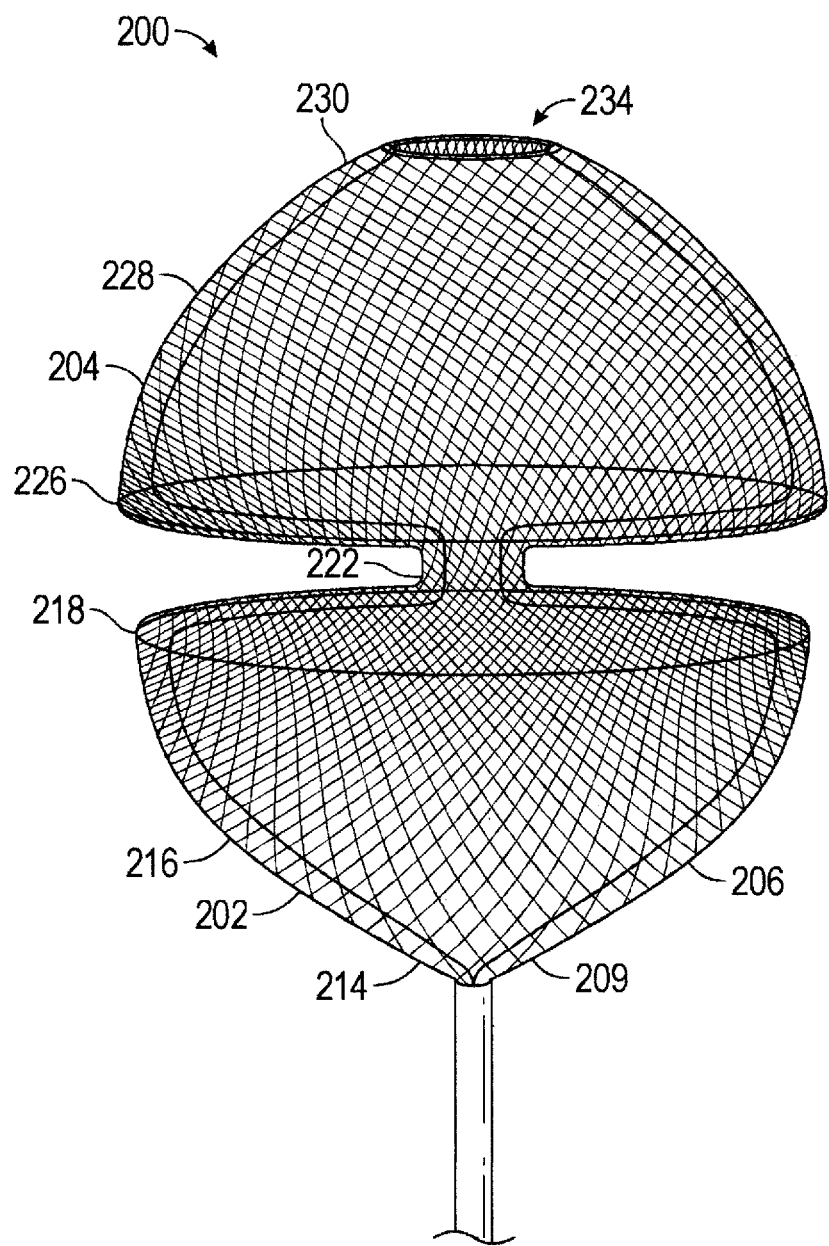
FIG. 1 is a perspective view of an occlusion device according to an embodiment of the present disclosure.

Aneurysms are abnormal bulging or weakening of a blood vessel, often an artery, and can have many complications. A bulging of the blood vessel can disrupt or put pressure on surrounding tissues. Cerebral aneurysms can result in a variety of side effects, such as impaired vision, impaired speech, impaired balance, etc. Further, the aneurysm creates a volume that is not along the main flow path of the blood through the blood vessel. It therefore can serve as a location for blood to become stagnant and, due to swirling eddy currents, can contribute to the formation of a thromboembolism. If an aneurysm ruptures, it can cause severe internal bleeding, which in cerebral arteries can often become fatal.

Aneurysms can be treated externally with open surgery. Such procedures typically involve closing off the entrance or "neck" of the aneurysm with a device such as vascular clip, clamp or a ligature. However, such open surgical procedures can be highly invasive and may lead to trauma to the adjacent tissue and other side effects.

Aneurysms can also be treated through endovascular procedures. In one procedure, detachable lengths of wires (e.g., coils) are inserted into the interior volume of the aneurysm using a catheter. The coils are intended to fill the volume of the aneurysm to decrease the flow of blood into the aneurysm, inducing stagnation of flow and stimulate clotting within the aneurysm. In settings of large cerebral aneurysms, filling of the aneurysm with multiple coils can lead to mass effect that may induce brain swelling and be an independent cause for new symptoms. In another procedure, for aneurysms with a relatively large neck, the adjunctive use of stents assists with the retention of the coils within the aneurysm. This approach may have a contraindication to being used when treating ruptured aneurysm, due to the need for additional anti-thrombotic medications. In another procedure, the coils are held in the volume of the aneurysm with a temporary balloon that is inflated in the blood vessel. The balloon is deflated and removed once the mass of coils is secured. In still another procedure, a stent device is placed in the artery to promote flow of blood past the aneurysm. This leads to stagnation of the blood within the aneurysm and thrombosis inside the aneurysm volume. However, a side branch of a main artery in which the stent device is placed may become trapped or "jailed," which can impede access to the side branch. In other instances, the side branch can become clotted off, possibly causing a stroke. Additionally, such a procedure generally requires the use additional anti-thrombotic medications, which limits the use of such devices in the setting of treatment of ruptured aneurysms. The stent device is often formed with a relatively tight weave. While the tight weave increases the effectiveness of the stent device in diverting the blood flow, it also impedes or prevents access to the volume of the aneurysm or the jailed artery. In the event that the aneurysm fails to clot, the obstruction of the aneurysm by the stent device prevents the possibility of placing embolic devices inside the aneurysm. Additional procedures such as the placement of additional stents or open surgery may then be required to treat the residual.

Procedures that involve packing the volume of the aneurysm can suffer from several common shortcomings. First, it can take many coils of wire to fill the volume of the aneurysm, which is time consuming and increases the time it takes to complete the procedure. Further, the coils may be compacted over time to occupy a smaller percentage of the total volume of the aneurysm. A great enough compaction of the coils can be considered a recurrence of the aneurysm and may require further treatment.

Figures 2, 3:
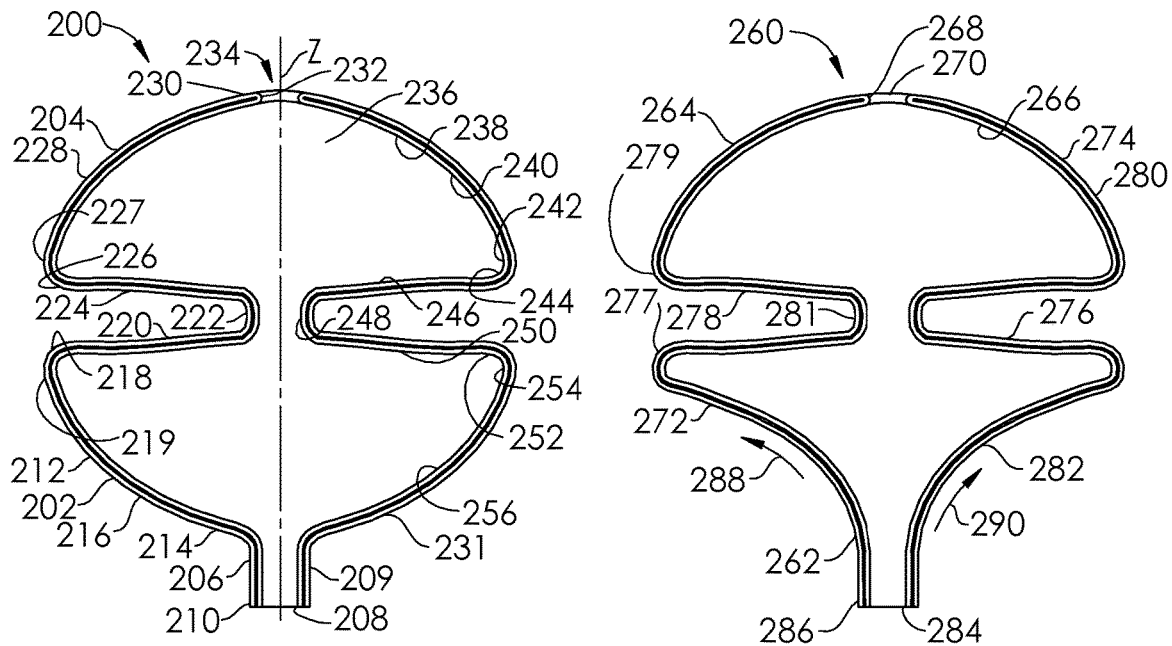
FIG. 2 is a sectional view of the occlusion device of FIG. 1.
FIG. 3 is a sectional view of an alternative occlusion device, according to an embodiment of the present disclosure.

FIG. 1 illustrates an occlusion device 200 configured for placement within an aneurysm. The occlusion device 200 comprises a proximal section 202 and a distal section 204, each constructed of a single, continuous dual layer mesh. Turning to FIG. 2, the occlusion device 200 is constructed from an inverted mesh tube 206 having a first end 208, a second end 210, and a wall 209. The inverted mesh tube 206 extends on an outer layer 212 from the second end 210 past a proximal end 214 of the proximal section 202 and along a proximal hemisphere shape 216 to a maximum diameter portion 218 having an acute angulation 219. From the maximum diameter portion 218, the outer layer 212 extends radially inward along a substantially flattened portion 220 to a central waist 222. The outer layer 212 then extends radially outward along a substantially flattened portion 224 of the distal section 204 to a maximum diameter portion 226 having an acute angulation 227 to a distal hemisphere shape 228 to a distal end 230 of the occlusion device 200. The hemisphere shape 228 is configured to contact at least a portion of an aneurysm dome. The maximum diameter portion 226 has a diameter that is about equal to the diameter of the maximum diameter portion 218, but in other embodiments, they may differ. The occlusion device 200 is substantially cylindrically symmetric around a central axis Z. However, in alternative embodiments, there may be certain portions of asymmetry, such as one or more indented or extended feature at a particular location in a perimeter. At the distal end 230, the wall 209 is inverted inwardly at an inversion fold 232, which creates a distal orifice 234 and an internal volume 236. The wall 209 transitions at the inversion fold 232 from the outer layer 212 to an inner layer 238 which follows the contours of the outer layer 212 from the distal orifice 234 to the first end 208. The inner layer 238 follows a hemisphere shape 240, a maximum diameter portion 242 having an acute angulation 244, a substantially flattened portion 246 of the distal section 204, a central waist 248, a substantially flattened portion 250 of the proximal section 202, a maximum diameter portion 252 having an acute angulation 254, and a hemisphere shape 256. The occlusion device 200 is fabricated as an inverted mesh tube 206 having a simple straight elongate configuration, and is subsequently formed into the shape shown in FIGS. 1 and 2 and heat set into this shape. For example, the occlusion device 200 may be constructed as a single layer mesh tube formed of at least some nickel-titanium alloy filaments, and then inverted on itself. The inverted mesh tube 206 may then be placed into a die or mold comprising one or more pieces, to hold it in the shape of the occlusion device 200. Then, the occlusion device 200 may be subjected to an elevated temperature and then cooled, to lock in the shape, resulting in an occlusion device 200 having at least some superelastic properties. Each of the proximal section 202 and distal section 204 are configured to be compressed or compacted within the lumen 148 of a delivery catheter 150 (e.g., microcatheter).

In some embodiments, one or both of the proximal section 202 or the distal section 204 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 200 to be visible on radiographs or fluoroscopy. The occlusion device 200 may be configured by controlling how much radiopaque material is used, by either the ratio of radiopaque filaments to non-radiopaque filaments, or by the amount of platinum core in the drawn filled tubes. In this manner, the occlusion device 200 can be selectively fabricated to be sufficiently visible, but not over visible, e.g., overly bright, such that other objects are obscured. In some embodiments, whether any of the filaments comprise radiopaque materials or not, a marker band may be attached to the proximal end 214 of the proximal section 202, by adhesive or epoxy bonding, or swaging, welding or other mechanical attachment.

FIG. 3 illustrates an occlusion device 260 also comprising an inverted mesh tube 262 and having an outer layer 264, an inner layer 266, and an inversion fold 268, which creates a distal orifice 270, and serves as the transition between the outer layer 264 and the inner layer 266. The inverted mesh tube 262 has a first end 284 and a second end 286. The occlusion device 260 includes a proximal section 272 and a distal section 274. The proximal section 272 and distal section 274 have substantially flattened portions 276, 278, and the distal section 274 has a distal hemisphere shape 280, configured to contact an aneurysm dome. There is a waist 281 between the substantially flattened portions 276, 278. The maximum diameter portion 279 has a diameter that is about equal to the diameter of the maximum diameter portion 277, but in other embodiments, they may differ. The proximal section 272 includes a concave cone shape 282, or circumferentially-extending concavity, which may be configured to direct blood flow, particularly when the occlusion device 260 is implanted within a bifurcation aneurysm or a terminal aneurysm, wherein the blood flow is directed along the paths of arrow 288 or arrow 290. The occlusion device 260 may comprise any of the materials and be made with any of the processes described in relation to the occlusion device 200.

Figures 4, 5:
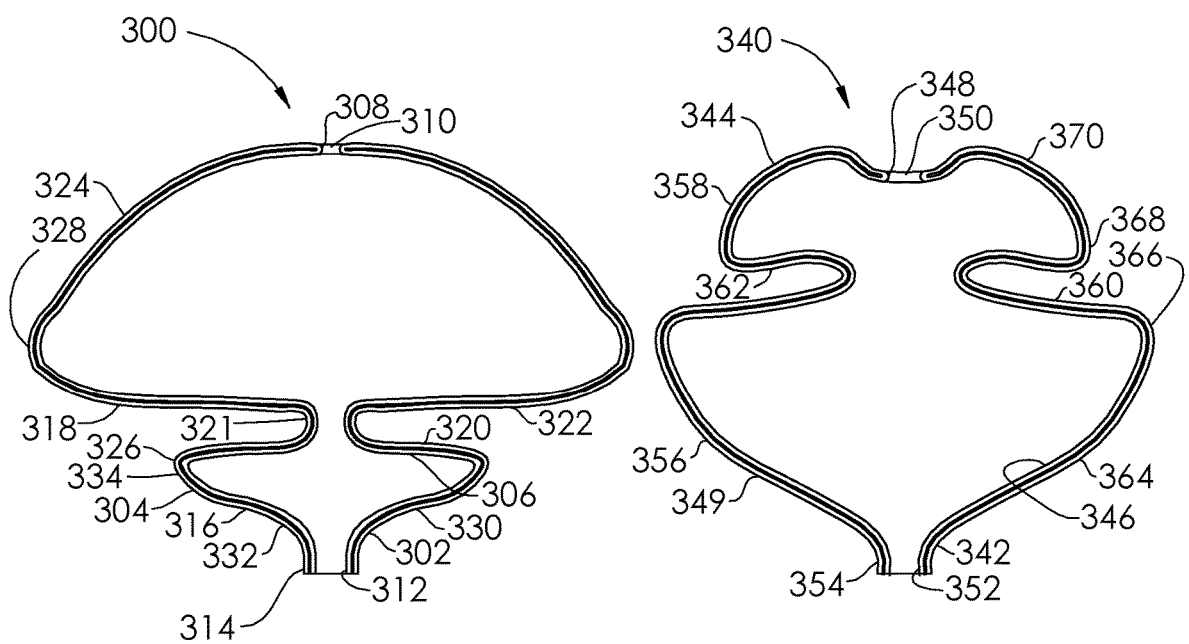
FIG. 4 is a sectional view of an alternative occlusion device, according to an embodiment of the present disclosure.
FIG. 5 is a sectional view of an alternative occlusion device, according to an embodiment of the present disclosure.

FIG. 4 illustrates an occlusion device 300 also comprising an inverted mesh tube 302 and having an outer layer 304, an inner layer 306, and an inversion fold 308, which creates a distal orifice 310, and serves as the transition between the outer layer 304 and the inner layer 306. The inverted mesh tube 302 has a first end 312 and a second end 314. The occlusion device 300 includes a proximal section 316 and a distal section 318. The proximal section 316 and distal section 318 have substantially flattened portions 320, 322, and the distal section 318 has a distal hemisphere shape 324, configured to contact an aneurysm dome. There is a waist 321 between the substantially flattened portions 320, 322. The maximum diameter portion 328, on the distal section 318, has a diameter that is larger than the diameter of the maximum diameter portion 326, on the proximal section 316, and thus, the occlusion device 300 is configured to be implanted in an aneurysm having a larger dome (distal) portion and a smaller proximal portion of the aneurysm sac. The proximal section 316 of the occlusion device 300 includes a partially convex, partially concave shape 330 which may be configured to direct blood flow along the concave portion 332, and also configured to interface with the proximal portion of the aneurysm at the convex portion 334. Both the concave portion 332 and the convex portion 334 face substantially proximally. The occlusion device 300 may comprise any of the materials and be made with any of the processes described in relation to the occlusion device 200.

FIG. 5 illustrates an occlusion device 340 also comprising an inverted mesh tube 342 and having an outer layer 344, an inner layer 346, and an inversion fold 348, which creates a distal orifice 350, and serves as the transition between the outer layer 344 and the inner layer 346. The inverted mesh tube 342 has a first end 352 and a second end 354. The occlusion device 340 includes a proximal section 356 and a distal section 358. The proximal section 356 and distal section 358 have curvilinear portions 360, 362 facing each other, and the proximal section 356 has a hemisphere shape 364, configured to contact a proximal wall of the aneurysm. The maximum diameter portion 368 of the distal section 358 has a diameter that is smaller than the diameter of the maximum diameter portion 366 of the proximal section 356, and thus, the occlusion device 340 is configured to be implanted in an aneurysm having a smaller dome (distal) portion and a larger proximal portion of the aneurysm sac. The distal section 358 includes a smaller hemisphere shape 370. The occlusion device 340 may comprise any of the materials and be made with any of the processes described in relation to the occlusion device 200.

Figure 6:
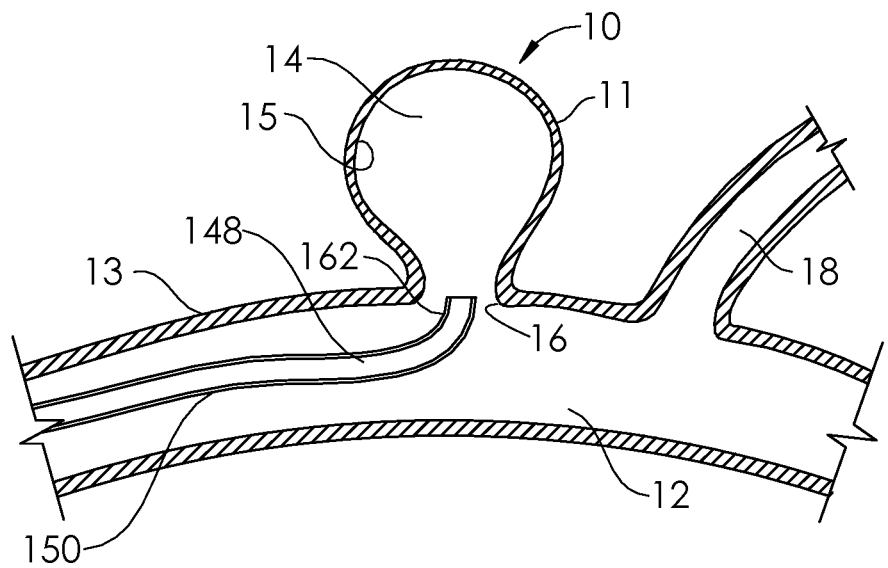
FIGS. 6-9 illustrate the implantation of the occlusion device of FIG. 1 in an aneurysm of a blood vessel of a patient.

In FIGS. 6-9, an aneurysm 10 having a neck portion 16 is shown. The occlusion device 200 is shown in use being implanted by a user (e.g., physician) into the aneurysm 10 through the delivery catheter 150 to disrupt or halt the flow of blood flow between the blood vessel 12 and the internal volume 14 of the aneurysm, thereby reducing the likelihood that the aneurysm 10 will rupture (or if previously ruptured, reducing the likelihood of rerupture). The occlusion device 200 is configured to be low profile device, minimizing disruptions to surrounding bodies, such as a side branch 18 of the blood vessel 12. The blood vessel 12 has a blood vessel wall 13 and the aneurysm 10 has an aneurysm wall 11. In FIG. 6, the delivery catheter 150 is advanced through a sheath and/or guiding catheter (not shown) through a puncture or cutdown in a peripheral blood vessel, such as a femoral artery, a brachial artery, or a radial artery. The distal end 162 of the delivery catheter 150 may be shaped with a curve, as shown, either by the manufacturer, or prior to the procedure by the user, in order to allow for improved backup support when delivering the occlusion device 200. The distal end 162 of the delivery catheter 150 is placed adjacent the neck portion 16 of the aneurysm 10. The delivery catheter 150 may be advanced over a guidewire (not shown) that is passed through the lumen 148. The guidewire may then be removed, leaving the lumen 148 as a delivery conduit and the delivery catheter 150 as a support column.

Figure 7:
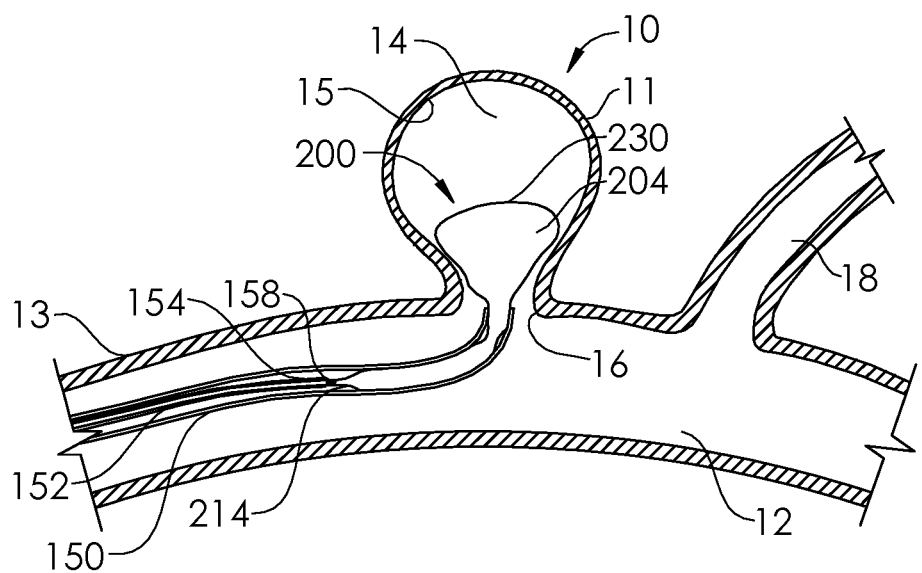
Figure 8:
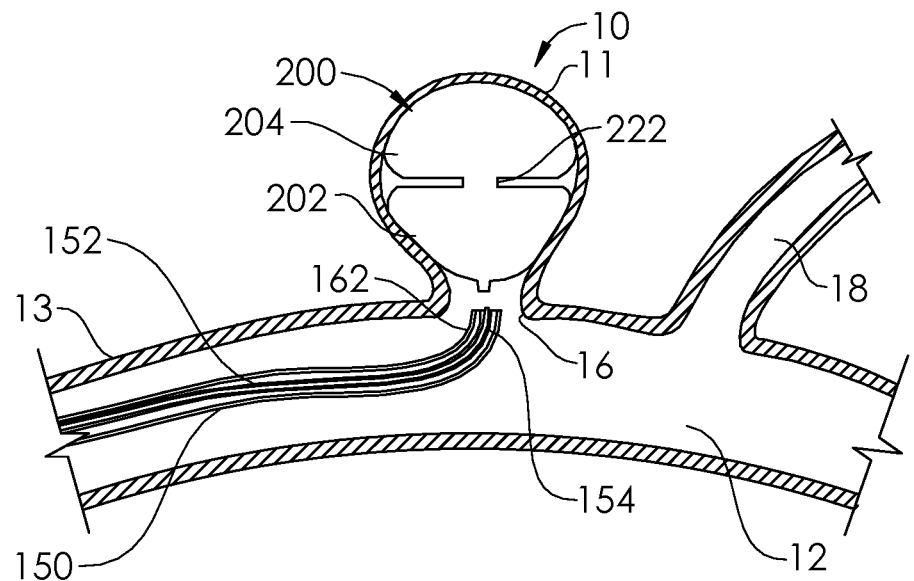

In FIG. 7, the occlusion device 200 is advanced through the lumen 148 of the delivery catheter 150, as described, and the distal section 204 of the occlusion device 200 is advanced out of the lumen 148 and into the internal volume 14 of the aneurysm 10. The distal end 230 is the first portion of the occlusion device 200 that exits the lumen 148 and thus is the first portion of the occlusion device to enter the aneurysm 10. The distal end 230 is blunt, soft, and atraumatic and is configured to first contact the interior surface 15 of the aneurysm 10. In FIG. 8, the occlusion device 200 is shown in a substantially expanded configuration within the internal volume 14 of the aneurysm 10. The proximal section 202 is expanded against the interior surface 15 of the aneurysm 10, and covers the neck portion 16 of the aneurysm. The distal section 204 is expanded against the interior surface 15 of the aneurysm 10, and serves to anchor or stabilize the proximal section 202 in the aneurysm 10 and adjacent the neck portion 16.

Figure 9:
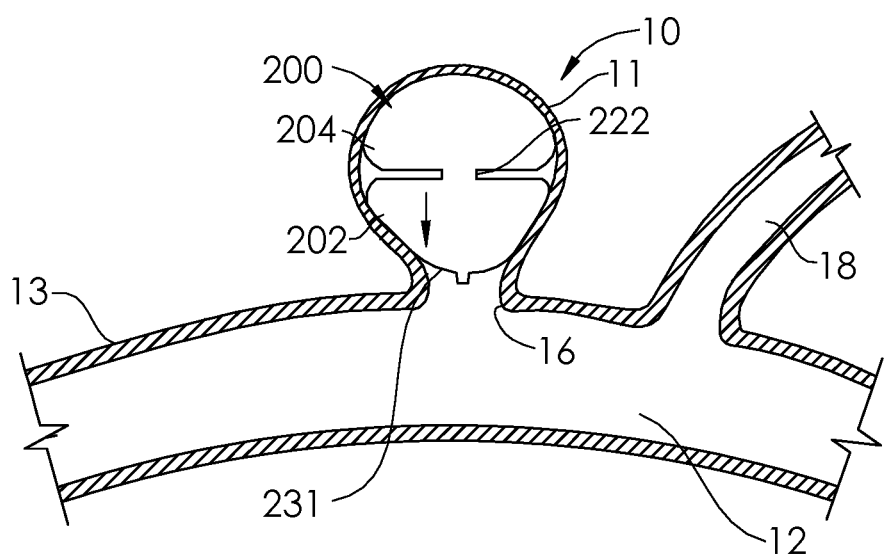
Figure 10:
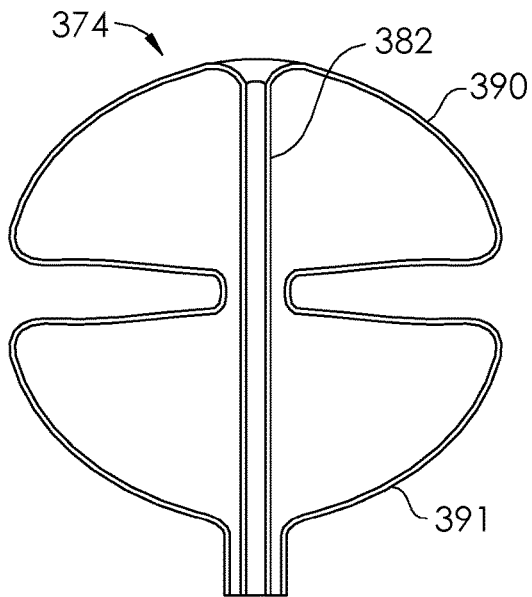
FIG. 10 is a sectional view of an alternative occlusion device, according to an embodiment of the present disclosure.
Figure 11:
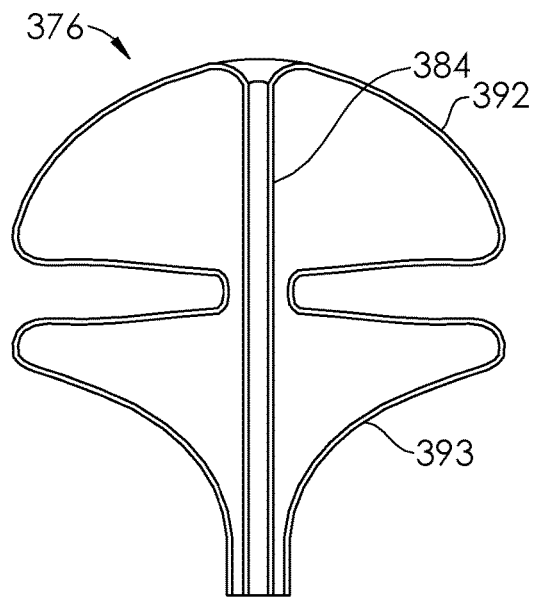
FIG. 11 is a sectional view of an alternative occlusion device, according to an embodiment of the present disclosure.
Figure 12:
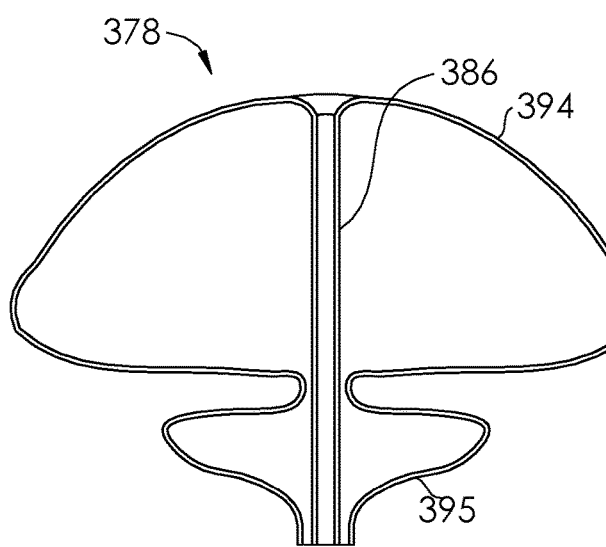
FIG. 12 is a sectional view of an alternative occlusion device, according to an embodiment of the present disclosure.
Figure 13:
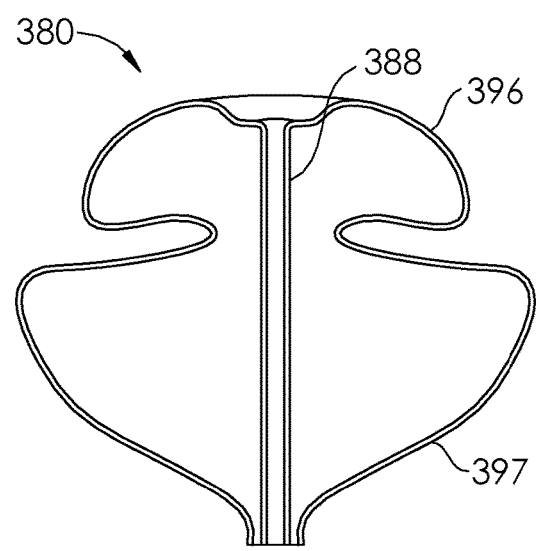
FIG. 13 is a sectional view of an alternative occlusion device, according to an embodiment of the present disclosure.

Also, in FIG. 8, the detachable joint 158 (see FIG. 7) has been detached, and thus, the free end 154 of the pusher 152 can be pulled into the lumen 148 of the delivery catheter 150. In some embodiments, the delivery catheter 150 is maintained over the detachable joint 158 during the detachment procedure, to further protect the aneurysm 10. In FIG. 9, the delivery catheter 150 is removed, and the deployed occlusion device 200 is in place to begin to occlude the internal volume 14 of the aneurysm. The distal section 204 also serves to force the proximal section 202 against the neck portion 16 and/or against the interior surface 15, see straight arrow in FIG. 9. The dual layer of mesh in the proximal section 202 at a lower portion 231 (FIGS. 2 and 9) aid in the disruption of blood flow into the aneurysm 10, thus causing thrombosis to isolate the internal volume 14 of the aneurysm 10 from blood flow through the blood vessel. 12. The waist 222 helps the distal section 204 transmit force to the proximal portion 202, though the maximum diameter portions 218, 226 are also configured to transmit force to the substantially flattened portions 220, 224, or the substantially flattened portions 220, 224 transmit to each other, as the waist 222 is longitudinally compressed. The force (straight arrow) maintaining the proximal section 202 in place, further assures this process, and also protects against undesired compaction over time of the occlusion device 200. The dual layers of mesh in the distal section 204 can aid in the healing of the dome. In an unruptured aneurysm, the contact with the dome can cause healing that can thicken the dome at this portion, where the dome is often at is thinnest, most stretched state. In a ruptured aneurysm, the contact with the dome can act like a bandage and accelerate or increase the healing process to further avoid a re-rupture.

The occlusion devices 260, 300, 340 of FIGS. 3-5 are implanted into aneurysms 10 in a similar manner to the occlusion device 200 described in relation to the implantation procedure of FIGS. 6-9. Alternative embodiments of the occlusion devices 200, 260, 300, 340 from FIGS. 1-5 are shown in FIGS. 10-13. Occlusion devices 374, 376, 378, 380 are each similar to occlusion devices 200, 260, 300, 340, respectively, except that the inner layers 382, 384, 386, 388 do not follow the contours of the outer layers 390, 392, 394, 396, but instead are substantially straight tubular columns. These columns may be the diameter of the original tubular mesh (as braided), or may be an expanded diameter (as heat formed). The inner layers 382, 384, 386, 388 can each provide additional column strength and longitudinal support, which can help to apply a force against the aneurysm neck portion 16 with the proximal sections 391, 393, 395, 39.

Figure 14:
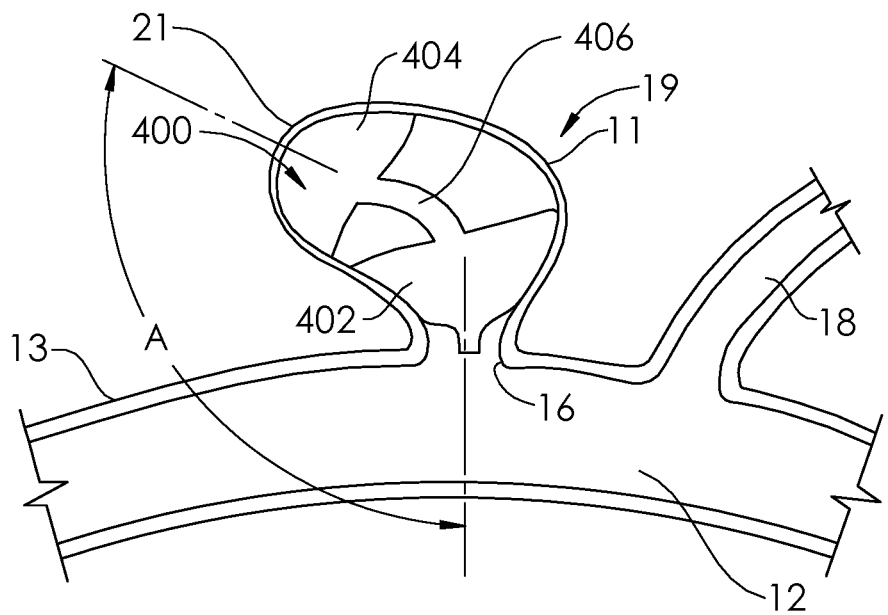
FIG. 14 is an occlusion device according to an embodiment of the present disclosure implanted within an aneurysm.

FIG. 14 illustrates an occlusion device 400 being implanted within an angulated sidewall aneurysm 19 having a dome 21 that is off axis from the neck portion 16. This may be approximated by angle A. The occlusion device 400 is similar to the occlusion device 200, and has a proximal section 402 that is separated from the distal section 404 by an elongate flexible extension 406. The flexible extension 406 may be similar to the central waist 222 of the occlusion device 200, but the diameter and the length may be varied in order to change its flexibility characteristics, and to change to total amount of angulation possible between the proximal section 402 and the distal section 404. The construction of the occlusion device 400 may be identical to any of the embodiments described in relation to the occlusion devices 200, 260, 300, 340, 374, 376, 378, 380 of FIGS. 2-5 and 10-13, however, the longer, more flexible extension 406 allows the distal section 404 to more readily angulate with respect to the proximal section 402. It also allows for a larger amount of angulation between the proximal section 402 and the distal section 404, because of the larger amount of space between them (e.g., because of increased longitudinal distance). Thus, the occlusion device 400 is capable conforming to a large number of different aneurysm shapes or aneurysm angular takeoff angles or general angulations. The occlusion device 400 may be configured to allow for an angle A of between 90° and 180°, or between about 135° and about 180°. Thus, the angle A is changeable to a minimum angle of between about 90 degrees and about 135 degrees. If the elongate flexible extension 406 is long enough, an angulation of less than 90° may even be possible, which might occur in some aneurysms with very odd shapes. The substantially flattened portions may have slight angulations or tapers, as do the substantially flattened portions 220, 224, 276, 278 of FIGS. 2-3 or those in 10-11, with the longitudinal space increasing toward the outer diameters, such that the angle A (FIG. 14) is decreased even further. The total longitudinal length of the flexible extension 406 can be between about 0.5 mm and about 30 mm, or between about 0.5 mm and about 25 mm, or between about 1 mm and about 10 mm, or between about 1 mm and about 6 mm, or between about 1 mm and about 3 mm. For cerebral aneurysms, the occlusion device 400 may be configured such that the proximal section 402 and the distal section 404 are each substantially hemispherical in shape, but that the flexible extension, when straight, provides an elongated, revolved oval profile. For example, with the proximal section 402 and the distal section 404 each having a hemisphere shape of about 6 mm in diameter, a 1 mm long flexible extension 406 begets a 7 mm long by 6 mm diameter implant. A 2 mm long flexible extension 406 begets an 8 mm long by 6 mm diameter implant. A 3 mm long flexible extension 406 begets a 9 mm long by 6 mm diameter implant. A wide range of sizes is possible, and the diameter of the proximal section 402 may differ from the diameter of the distal section 404 or they may be substantially the same as each other.

Figure 15:
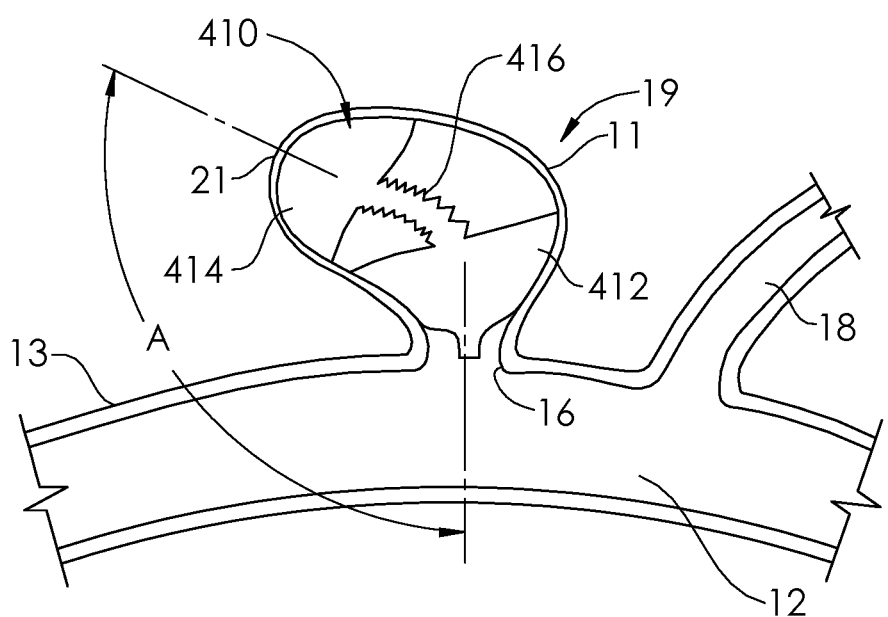
FIG. 15 is an occlusion device according to an embodiment of the present disclosure implanted within an aneurysm.
Figure 16:
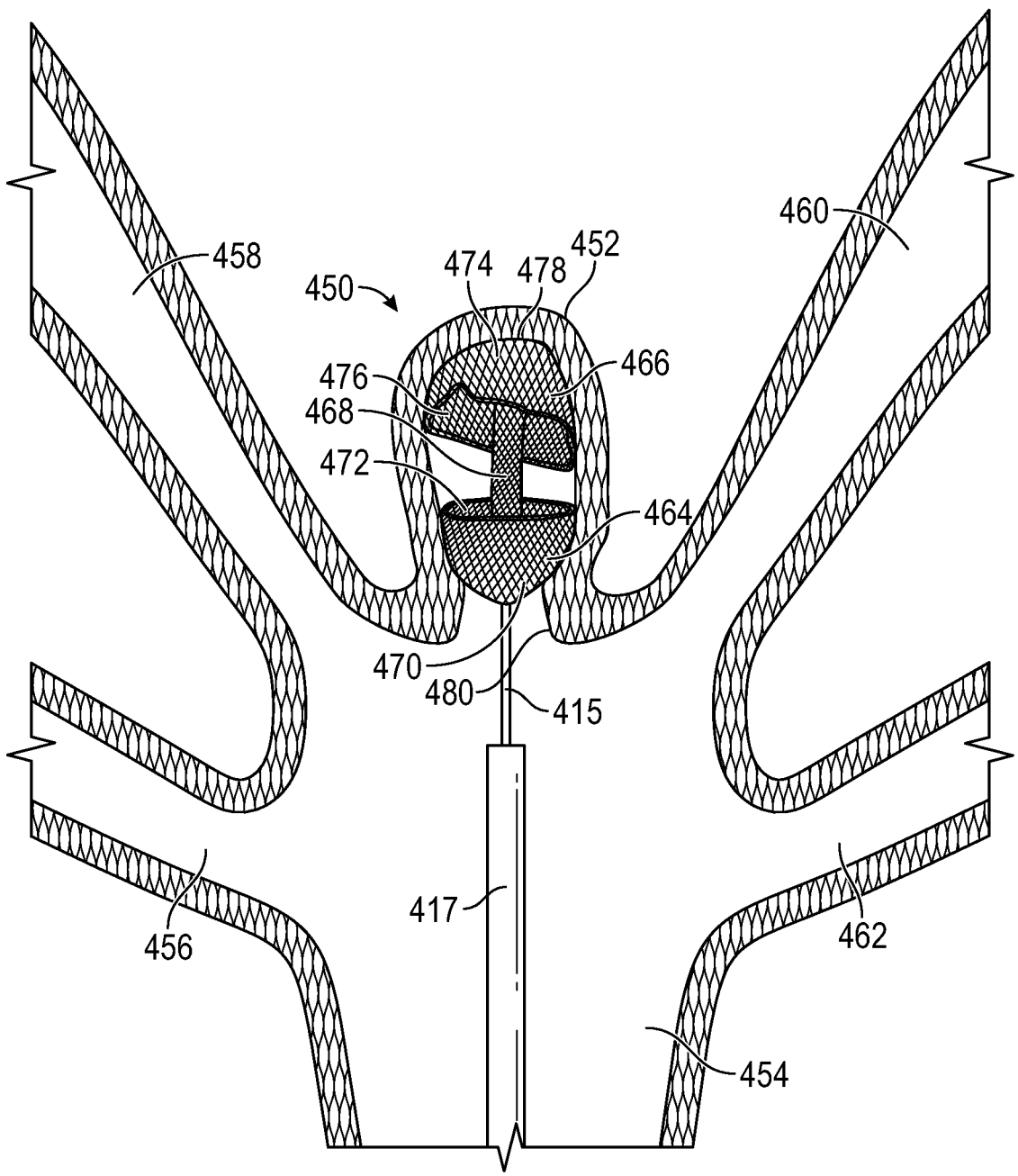
FIG. 16 illustrates an occlusion device according to an embodiment of the present disclosure implanted within an aneurysm.

FIG. 15 illustrates an occlusion device 410 implanted within an angulated sidewall aneurysm 19 via a delivery catheter 417. The occlusion device 410 is similar to the occlusion device 400 of FIG. 14, except the elongate extension 416, extending between the proximal section 412 and the distal section 414, has a bellows configuration that further aids its bendability. Both the inner and outer layer of the mesh tube may include the bellows-type feature, or only the outer layer may include this feature. In alternative embodiments, the flexible section 406 or elongate extension 416 (e.g., comprising a bellows-type feature) can have an outer diameter that varies along its longitudinal axis. For example, the outer diameter may get gradually smaller in the center and larger on the ends and thus have a concave cylindrical shape or hourglass shape. Alternatively, the outer diameter may get gradually larger in the center and smaller on the ends and thus have a convex cylindrical shape or American football shape. FIG. 16 illustrates an occlusion device 450 implanted within an aneurysm 452. The aneurysm 452 is terminal to a main artery 454, and several connecting arteries 456, 458, 460, 462. The occlusion device 450 of FIG. 16 has a proximal section 464 and a distal section 466, separated by an elongated flexible extension 468. The proximal section 464 includes a hemispheric proximal end 470 and a concavity 472 distally, opposite the proximal end 470. The distal section 466 includes a hemispheric distal end 474 and a concavity 476 proximally, opposite the distal end 474. The distal section 466 and the proximal section 464 are each able to pivot (away from the longitudinal axis) in relation to the elongated flexible extension 468, which allows the occlusion device 450, when delivered into the aneurysm 452, to conform to the shape of the inner contours of the aneurysm 452, and thus more snugly fit into the aneurysm 452. As shown in FIG. 16, an apex 478 the distal section 466 of the occlusion device 450 is slightly pivoted back, and to the right. The proximal section 464 is slightly pivoted forward. The proximal section 464 has a maximum diameter that is larger than the diameter or transverse dimension of the aneurysm neck 480. The maximum diameter of the proximal section 464 may also be configured to be oversized in relation to the aneurysm sac, in order to apply a gripping radial force. The same is true of the distal section 466. Once in the preferred position within the aneurysm 452, the occlusion device 450 is then detached from the pusher 415.

Figure 17:
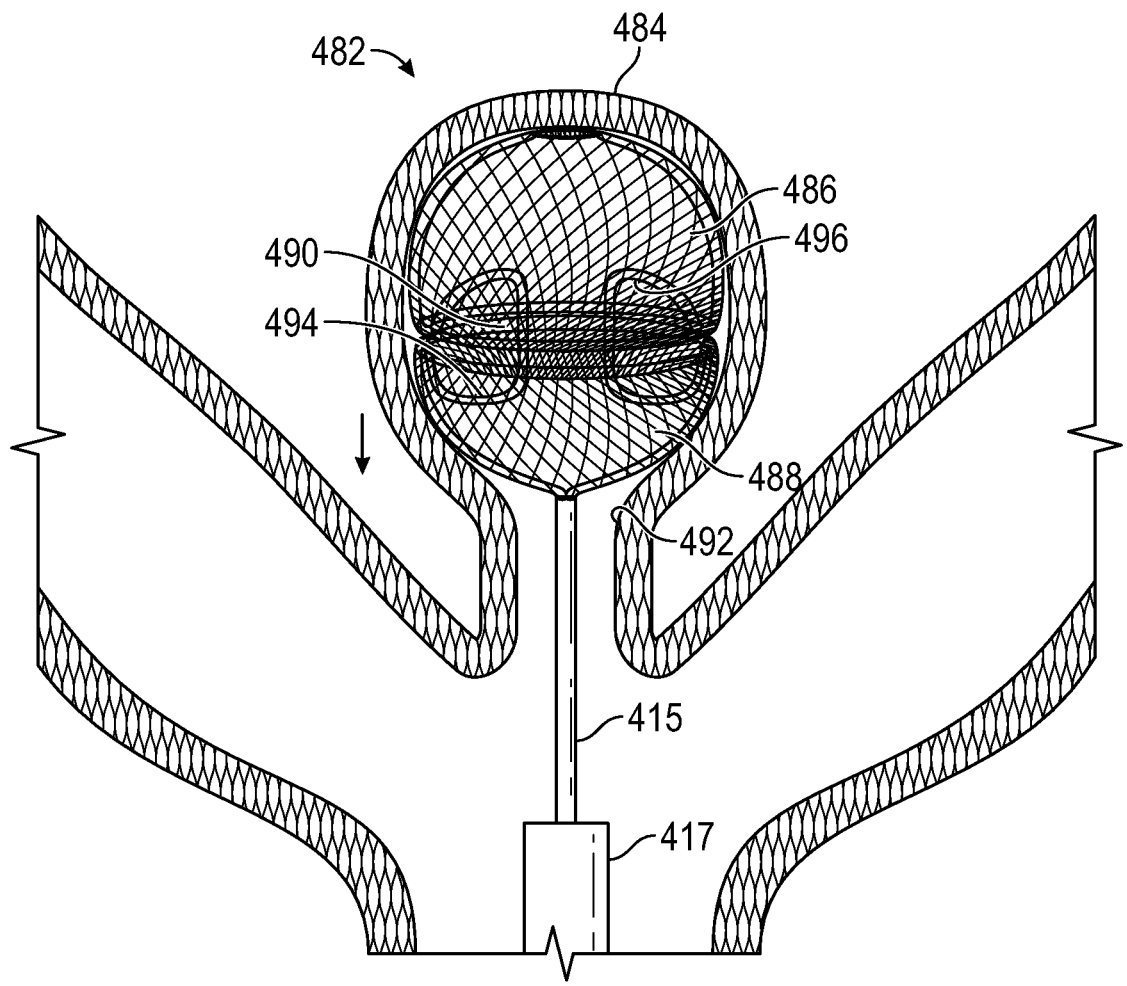
FIG. 17 illustrates an occlusion device according to an embodiment of the present disclosure implanted within an aneurysm
Figure 18:
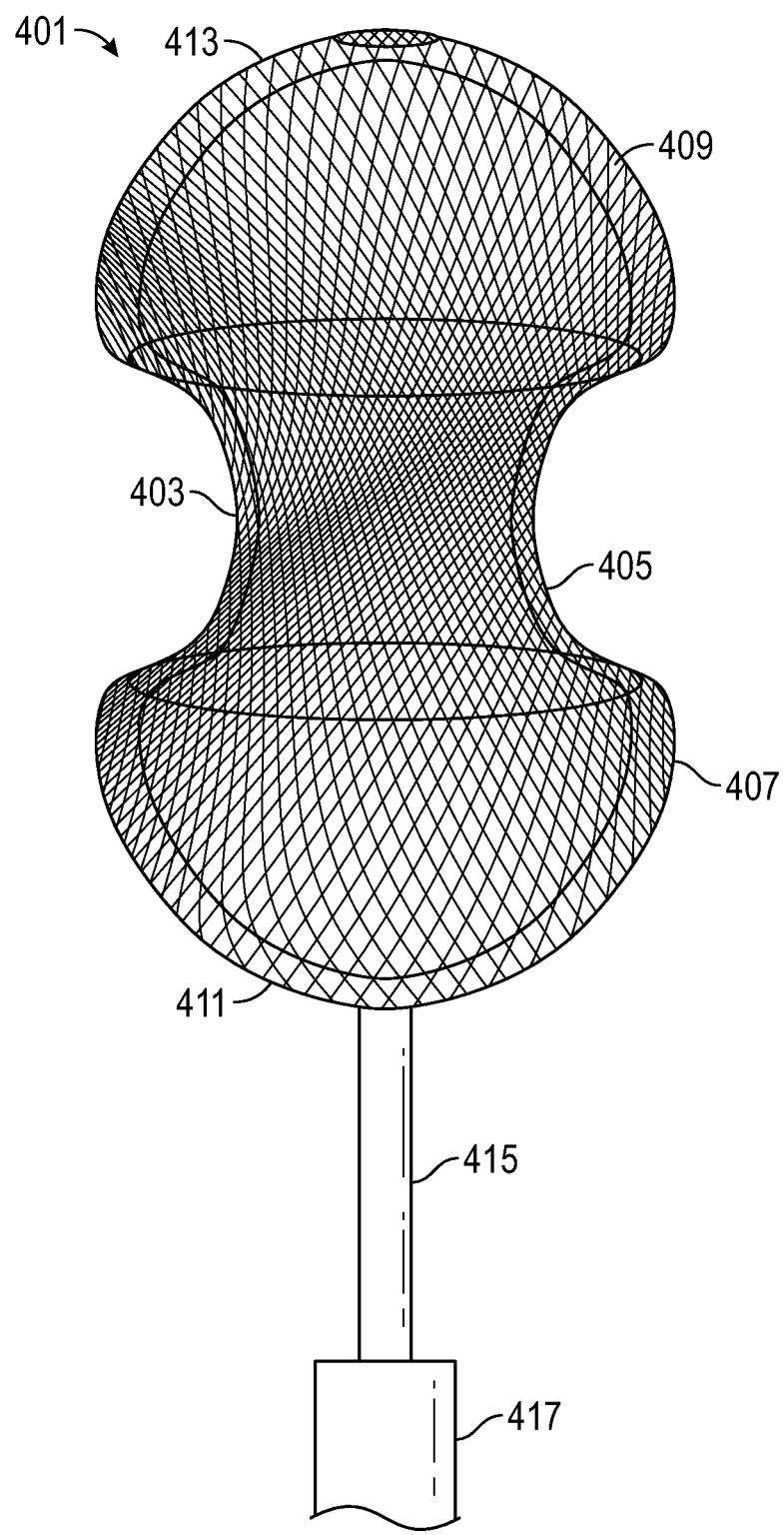
FIG. 18 illustrates an occlusion device according to an embodiment of the present disclosure.
Figure 19:
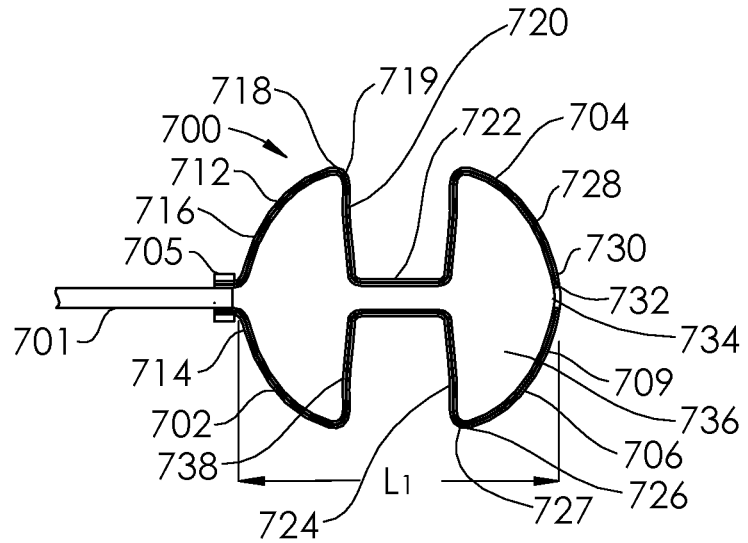
FIG. 19 is a sectional view of an unrestrained occlusion device according to an embodiment of the present disclosure.
Figure 20:
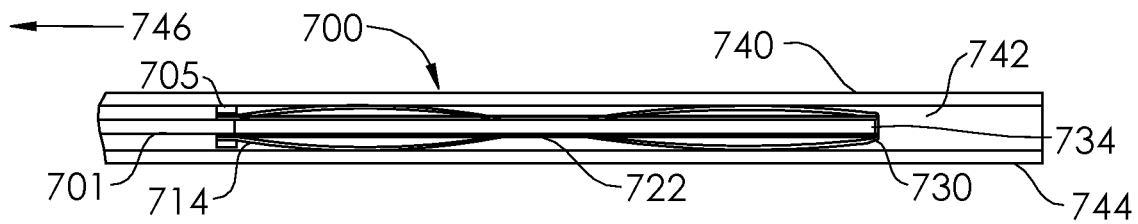
FIG. 20 is the occlusion device of FIG. 19 restrained within a delivery catheter.
Figure 21:
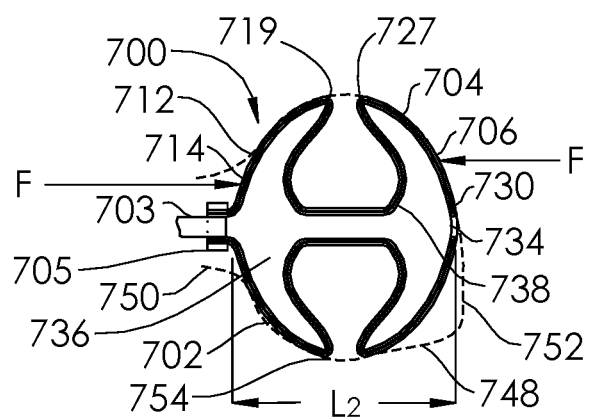
FIG. 21 is the occlusion device of FIG. 19 restrained within an aneurysm.

FIG. 17 illustrates an occlusion device 482 being implanted within an aneurysm 484. The occlusion device 482 of FIG. 17 is similar to the occlusion device 200 of FIGS. 1-2, but has slightly different dimensions. As the occlusion device 482 is implanted within the aneurysm, the distal section 486 and the proximal section 488 are compressed longitudinally together. The waist 490 is able to deform somewhat (e.g., shorten and widen) to allow the dynamic shaping of the occlusion device 482 to occur when implanted into the aneurysm 484. The proximal section 488 is forced (straight arrow) against the neck 492. The substantially flattened portion 494 of the proximal section 488 and the substantially flattened portion 496 of the distal section 486 are each able to flex to form ring-shaped concavities. The flexing acts as a spring, to maintain the force of the proximal section 488 against the neck 492. An occlusion device 401 having a relatively wider waist 403 and relatively longer flexible extension 405 between its proximal section 407 and its distal section 409. is shown in FIG. 18. The waist 403 of the occlusion device of FIG. 18 has a circumferentially extending concavity (hourglass shape) and comprises a hemispherical proximal face 411 and a hemispheric distal face 413. The occlusion devices of FIGS. 16-18 are shown still coupled to the pusher 415 and being delivered through a delivery catheter 417. FIGS. 19-21 illustrate three different configurations of an occlusion device 700. In FIG. 19, the occlusion device, as heat-formed, is in a completely unrestrained, expanded configuration. In FIG. 20, the occlusion device is constrained within a microcatheter lumen 742. In FIG. 21, the occlusion device has been delivered into an aneurysm 748.

FIG. 19 illustrates an occlusion device 700 comprising a proximal section 702 and a distal section 704 and a waist 722, all constructed of a single, continuous dual layer mesh. The occlusion device 700 is constructed from an inverted mesh tube 706 having a first end, a second end, and a wall (as in the occlusion device of FIGS. 1-2). The inverted mesh tube 706 extends on an outer layer 712 past a proximal end 714 of the proximal section 702 and along a hemisphere shape 716 to a maximum diameter portion 718 having an acute angulation 719. From the maximum diameter portion 718, the outer layer 712 extends radially inward along a substantially flattened portion 720 to the central waist 722. The outer layer 712 then extends radially outward along a substantially flattened portion 724 of the distal section 704 to a maximum diameter portion 726 having an acute angulation 727 to a hemisphere shape 728 to a distal end 730 of the occlusion device 700. The hemisphere shape 728 is configured to contact at least a portion of an aneurysm dome. The maximum diameter portion 726 has a diameter that is about equal to the diameter of the maximum diameter portion 718, but in other embodiments, they may differ. At the distal end 730, the wall 709 is inverted inwardly at an inversion fold 732, which creates a distal orifice 734 and an internal volume 736. The wall 709 transitions at the inversion fold 732 from the outer layer 712 to an inner layer 738 which follows the contours of the outer layer 712 from the distal orifice 734 to the first end. The occlusion device 700 is shown coupled to an elongate pusher 701 and a marker band 705.

In FIG. 19, the occlusion device 700 is shown unrestrained. Thus, if the mesh tube 706 is formed of at least some nickel-titanium, or shape memory alloy, filaments, braided together, the shape shown in FIG. 19 can be heat formed, as described herein. The occlusion device 700, in its compressed configuration, is shown in FIG. 20, inserted through the lumen 742 of a delivery catheter 740 having a distal end 744 and a proximal end 746. FIG. 21 shows the occlusion device 700 within an aneurysm 748 having a neck 750 and a dome 752. The proximal section 702 and a distal section 704 are each deformed from contact with the aneurysm wall 754, thus confirming to the aneurysm wall 754 in a snug manner. The overall length $L_2$ of the occlusion device 700 becomes less than the original length $L_1$ (FIG. 19)

because of longitudinal compressive forces F applied in return by the aneurysm wall 754. Thus, the overall shape of the occlusion device within the aneurysm 748 in FIG. 21 becomes more spherical than that of the unrestrained shape in FIG. 19. The proximal end 714 and the marker band 705 are at or adjacent the neck 750 of the aneurysm 748, while the distal section 704 is adjacent the dome 752. FIG. 21 also shows a remnant 703 of the pusher 701 after detachment has occurred. In some embodiments, no remnant of the pusher 701 remains after detachment. The occlusion device 700 is very conformable with different aneurysmal shapes and sizes. Because of this, the occlusion device 700 may also fit into an aneurysm that is longitudinally longer and diametrically narrower than the aneurysm 748 of FIG. 21. It may also fit into an aneurysm that has a significantly non-symmetric shape.

Figure 22:
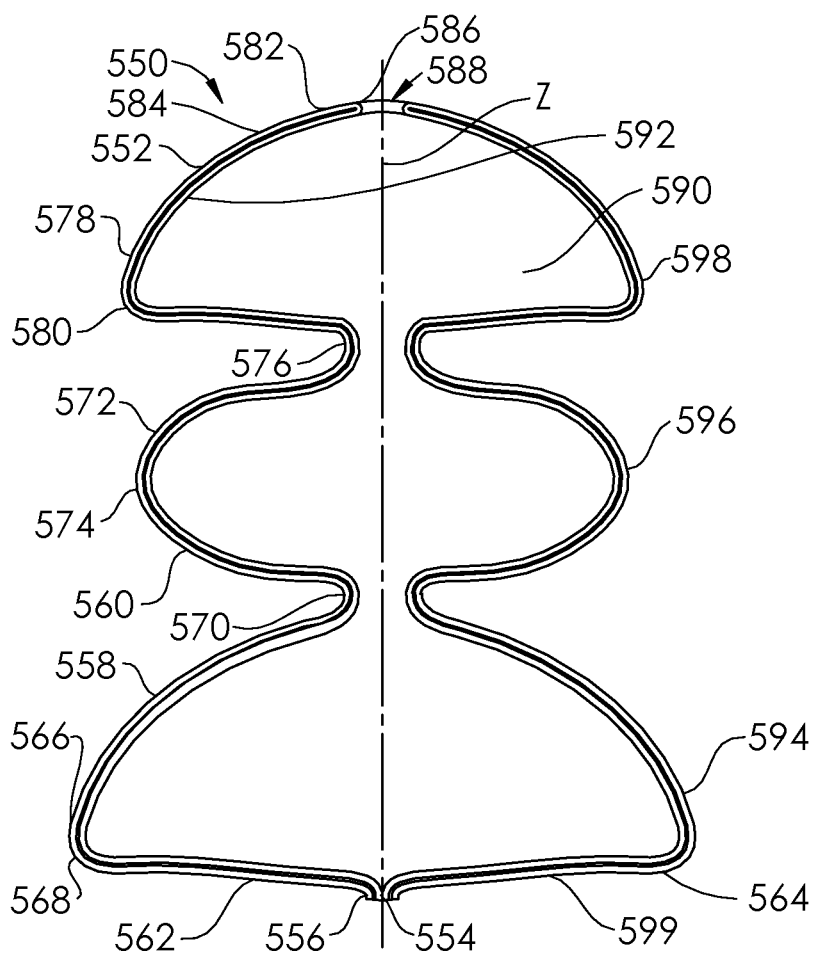
FIG. 22 is a sectional view of an occlusion device according to an embodiment of the present disclosure.

Turning to FIG. 22, an occlusion device 550 is constructed from an inverted mesh tube 552 having a first end 554, a second end 556, and a wall 558. The inverted mesh tube 552 extends on an outer layer 560 from the second end 556 past a proximal end 562 of the proximal section 564 and along a lower mushroom shape 566 to a maximum diameter portion 568. From the maximum diameter portion 568, the outer layer 560 extends radially inward along the mushroom shape 566 to a first central waist 570. The outer layer 560 then extends radially outward along a globular portion 572 having a maximum diameter potion 574 and then to a second central waist 576. Though the globular portion 572 of the occlusion device 550 is relatively short and wide, in other embodiments, the opposite might be true, with the globular portion 572 having more of an American football shape. In other embodiments, the globular portion 572 may have a generally spherical shape. The outer layer 560 then forms an upper mushroom shape 578 having a maximum diameter 580 to a distal end 582 of the occlusion device 550. The hemisphere shape 584 of the upper mushroom shape 578 is configured to contact an aneurysm dome. The maximum diameter 580 is about equal to the maximum diameter 574, but in other embodiments, they may differ. The occlusion device 550 is substantially cylindrically symmetric around a central axis Z. However, in alternative embodiments, there may be certain portions of asymmetry, such as one or more indented or extended feature at a particular location in a perimeter. At the distal end 582, the wall 558 is inverted inwardly at an inversion fold 586, which creates a distal orifice 588 and an internal volume 590. The wall 558 transitions at the inversion fold 586 from the outer layer 560 to an inner layer 592 which follows the contours of the outer layer 560 from the distal orifice 588 to the first end 554. The occlusion device 550 is fabricated as an inverted mesh tube 552 having a simple straight elongate configuration, and is subsequently formed into the shape shown in FIG. 22 and heat set into this shape. Each of the three sections, a proximal section 594, a central section 596, and a distal section 598, are shown in FIG. 22 in their expanded configurations, but are configured to be compressed or compacted within the lumen 148 of a delivery catheter 150 (e.g., microcatheter). The proximal end 562, located on the lower portion of the proximal section 594 has a flat surface 599 or substantially flat surface, and is configured for engaging, and even gripping, the aneurysm neck at the interior portion of the aneurysm. The engagement of the aneurysm neck by the flat surface 599 or substantially flat surface may help seal the aneurysm and help prevent an endoleak. The globular portion 572/central section 596 is configured to allow the angulation between the proximal section 594 and the distal section 598, while providing some body, or a stop/limit in between.

In some embodiments, one or more of the proximal section 594, central section 596, or distal section 598 may comprise some nickel-titanium alloy filaments and some radiopaque elements, comprising platinum, gold, tantalum, or alloys of any of these or other radiopaque materials. In some embodiments, the filaments may comprise drawn filled tubes, such as those comprising a nickel-titanium alloy outer wall and a platinum core. The radiopaque material allows the occlusion device 550 to be visible on radiographs or fluoroscopy. The occlusion device 550 may be configured by controlling how much radiopaque material is used, by either the ratio of radiopaque filaments to non-radiopaque filaments, or by the amount of platinum core in the drawn filled tubes. In this manner, the occlusion device 550 can be selectively fabricated to be sufficiently visible, but not over visible, e.g., overly bright, such that other objects are obscured. In some embodiments, whether any of the filaments comprise radiopaque materials or not, a marker band may be attached to the first end 554 and/or second end 556 of the inverted mesh tube 552, by adhesive or epoxy bonding, or swaging, welding or other mechanical attachment.

Figure 23:
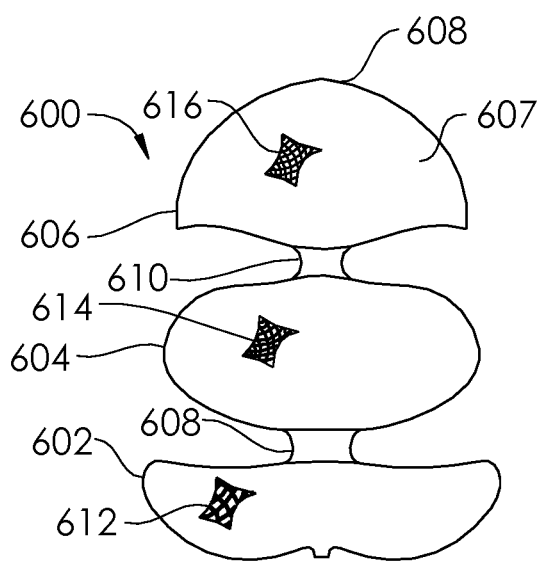
FIG. 23 is a side view of an occlusion device according to an embodiment of the present disclosure.

FIG. 23 illustrates an occlusion device 600 having an inverted mushroom-shaped proximal section 602, a globular central section 604, and a mushroom-shaped distal section 606 having a distal apex 608. Each of the sections 602, 604, 606 are separated by central waists 608, 610. Sections 602, 604 are separated by central waist 608 and sections 604, 606 are separated by central waist 610. Each of the sections 602, 604, 606 are formed from braided mesh 607 having different stiffness characteristics from each other. Though the sections 602, 604, 606 are fully braided, the braiding is only shown in windows 612, 614, 616 for simplicity. The proximal section 602 is braided such that it is stiffer than either the central section 604 or the distal section 606. The proximal section 602 may be braided by larger diameter filaments, and/or may be braided with larger braid angles, to achieve the increased stiffness. The increased stiffness is configured for securely wedging or setting against the aneurysm neck, for example, to achieve better closure or disruption at the entry to the aneurysm. The distal section 606 is braided such that it is less stiff/more flexible than either the central section 604 or the proximal section 602. The distal section 606 may be braided by smaller diameter filaments, and/or may be braided with smaller braid angles, to achieve the decreased stiffness. The decreased stiffness is configured for softly setting against the aneurysm dome. This is particularly helpful in avoiding a rupture of an aneurysm, for example, a high-risk aneurysm. A high-risk aneurysm may have a substantially large diameter, or a substantially thin wall at the dome. Another high-risk aneurysm may be a previously ruptured aneurysm that has at least partially healed, but which may be prone to rerupture. The central section 604 may be braided by filaments, and/or may be braided with braid angles, that achieve an intermediate stiffness to the proximal section 602 and the distal section 606. Changes in wire/filament diameter may be created after forming the braided mesh 607 from a single set of wires, by adjusting or rearranging the braid crossings. In some embodiments, the distal section 606 may be subsequently etched (chemical etch, photochemical etch) to decrease the overall wire diameter and decrease the stiffness. In some embodiments, both the distal section 606 and the central section 604 are etched in a first etching operation. Then, only the distal section 606 is etched in a second etching operation. This, as originally formed, the proximal section 602, central section 604, and distal section 606 are formed from wires having the same diameter, but after the two etching operations, the distal section 606 has smaller diameter wires than the central section 604 and the central section 604 has smaller diameter wires than the proximal section 602. Thus, in some embodiments, the distal section 606 may be made more flexible than the proximal section 602 via etching alone.

Figure 24:
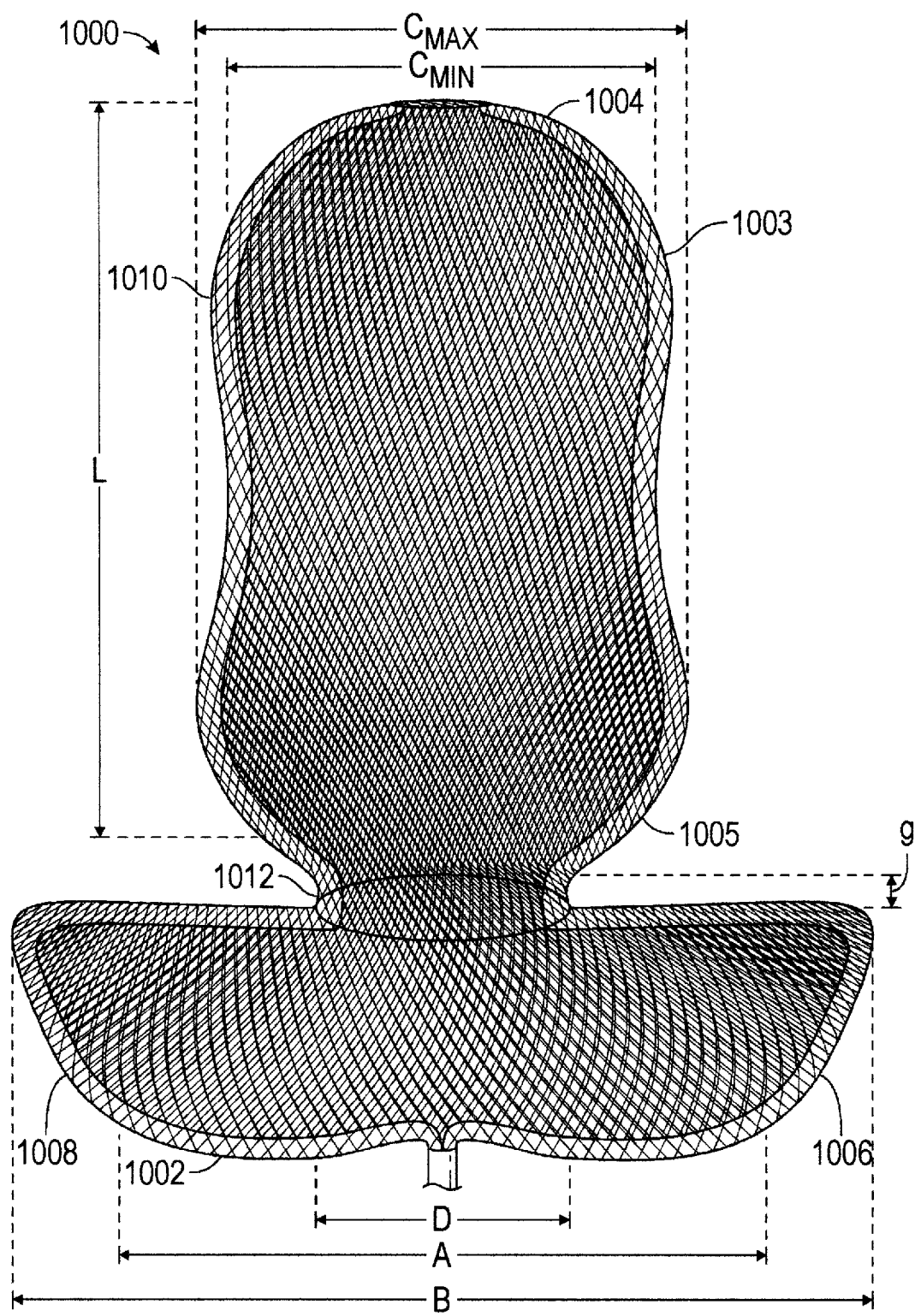
FIG. 24 is a plan view of an occlusion device according to an embodiment of the present disclosure.

FIG. 24 illustrates an occlusion device 1000 having a proximal end 1002 and a distal end 1004 and configured for placement within an aneurysm. The occlusion device 1000 comprises a lower portion 1006 having a proximal outer diameter A and a distal outer diameter B and a tapered frustoconical section 1008 extending between diameter A and diameter B. In some embodiments, the lower portion 1006 is circular, with substantially the same diameter at any transverse slice (around the perimeter). In other embodiments, the lower portion 1006 is non-circular, and may comprise an ellipse, an oval, a polygon or other shapes. The tapered frustoconical section 1008 is configured to be larger than a maximum transverse dimension of an opening into the aneurysm (the neck portion) at at least some portion between A and B. In some embodiments, the diameter A is configured to be larger than a maximum transverse dimension of an opening into the aneurysm (the neck portion). Thus, the lower portion 1006 is configured to completely cover the neck portion, and thus to cause stagnation of blood within the aneurysm, leading to occlusion. The occlusion device 1000 is constructed from a mesh (braided) Nitinol (nickel-titanium alloy) tube 1005 that is inverted on itself. The mesh tube 1005 has a first end and a second end. The second end is folded back over the outer diameter of the first end thus providing an outer facing surface 1003 and an inner facing surface (not visible in FIG. 24). The mesh tube 1005 is heat-formed such that the occlusion device 1000 comprises several expanded portions: the lower portion 1006, an upper portion 1010, and an intermediate waist portion 1012. The upper portion 1010 has a length L, a maximum diameter CMAX and a minimum diameter CMIN. The waist portion 1012 has a diameter D and a length g.

Particular ratios of the dimensions of the occlusion device 1000 have been found to be effective in creating a simple, easily-formed structure (body) that is particularly suited to be placed within aneurysms that may have at least one elongated dimension. For example, an aneurysm that is deep and narrow, or an aneurysm that is wide and short. The length of L of the upper portion 1010 may range from between about 1 mm to about 25 mm. The diameter C may range from between about 1 mm and about 25 mm. The diameter B may range from between about 1 mm and about 25 mm. The diameter A may range from between about 1 mm and about 24 mm. Generally, the diameter C is between about 50% to about 100% of the diameter B. Furthermore, generally, the diameter A is between about 50% to about 100% of the diameter B. In some embodiments, the diameter A is between about 70% and about 90% of the diameter B.

As formed (e.g., heat-formed), the occlusion device 1000 has an expanded configuration (shown in FIG. 24) and a collapsed configuration, configured for delivery through the lumen of a delivery catheter (e.g., microcatheter). The occlusion device 1000 comprises two mesh layers, provided by the outer facing surface 1003 and the inner facing surface. In some embodiments, the occlusion device 1000 may comprise some nickel-titanium alloy filaments and some radiopaque elements, comprising platinum, gold, tantalum, or alloys of any of these or other radiopaque materials. In some embodiments, the filaments may comprise drawn filled tubes (DFT), such as those comprising a nickel-titanium alloy outer wall and a platinum core. The radiopaque material allows the occlusion device 1000 to be visible on radiographs or fluoroscopy. The occlusion device 1000 may be configured by controlling how much radiopaque material is used, by either the ratio of radiopaque filaments to non-radiopaque filaments, or by the amount of platinum core in the drawn filled tubes. In this manner, the occlusion device 1000 can be selectively fabricated to be sufficiently visible, but not over visible, e.g., overly bright, such that other objects are obscured. In some embodiments, whether any of the filaments comprise radiopaque materials or not, a marker band may be attached to the proximal end 1002 of the occlusion device 1000, by adhesive or epoxy bonding, or swaging, welding or other mechanical attachment. The drawn filled tubes (DFT) may each have a platinum core that has a cross-sectional area that is between about 10% and about 70% of the total cross-sectional area of the DFT. In some embodiments, all (100%) of the filaments may comprise DFTs. In other embodiments, between 50% and 100% of the filaments may comprise DFTs, with the remainder of the filaments comprising only nickel-titanium alloy.

Turning to FIG. 25, the occlusion device 1000 may be coupled at or near its proximal end 1002 to a pusher 152, having a distal end 154 and a proximal end 156. The pusher 152 may comprise a wire, a hypo tube, or another elongate structure having column support is detachably coupled at its distal end 154 to the proximal end 1002 of the occlusion device 1000. A detachable joint 158 may comprise one of a number of detachment systems, including but not limited to pressurized detachment, electrolytic detachment mechanisms, hydraulic detachment mechanisms, mechanical or interlocking detachment mechanisms, chemical detachment mechanisms, heat-activated detachment systems, or frictional detachment systems. In any of the embodiments disclosed herein, alternative detachable joint may be employed, such as the detachable joints disclosed in co-pending U.S. patent application Ser. No. 16/840,410, filed on Apr. 5, 2020, and entitled "Systems and Methods for Treating Aneurysms" and in co-pending U.S. patent application Ser. No. 16/840,412, filed on Apr. 5, 2020, and entitled "Systems and Methods for Treating Aneurysms," both of which are hereby incorporated by reference in their entirety for all purposes. During delivery, the pusher 152 is held on its proximal end 156 by a user and pushed in a forward longitudinal direction in order to advance the occlusion device 1000 to the distal end of a delivery catheter (e.g., a microcatheter) having a delivery lumen. The delivery catheter may also include a proximal hub, such as a luer connector.

FIG. 26 illustrates a first view of the occlusion device 1000 delivered into a first aneurysm configuration 1020 comprising an aneurysm 1022, a neck 1024, a first parent vessel arm 1026, a second parent vessel arm 1028, and an additional connecting vessel 1030. FIG. 27 illustrates a different view. The waist portion 1012 allows some flexure between the upper portion 1010 and the lower portion 1006, and thus the upper portion 1010 is able to be somewhat compressed into the lower portion 1006, as seen in FIGS. 26 and 27. Thus, the lower portion 1006 protects and covers the neck 1024 of the aneurysm 1022 while the upper portion 1010 allows the occlusion device 1000 to adapt to the shape of the aneurysm 1022 for a snug by safe fit. The waist portion 1012 also acts as a shock absorber.

Figure 28:
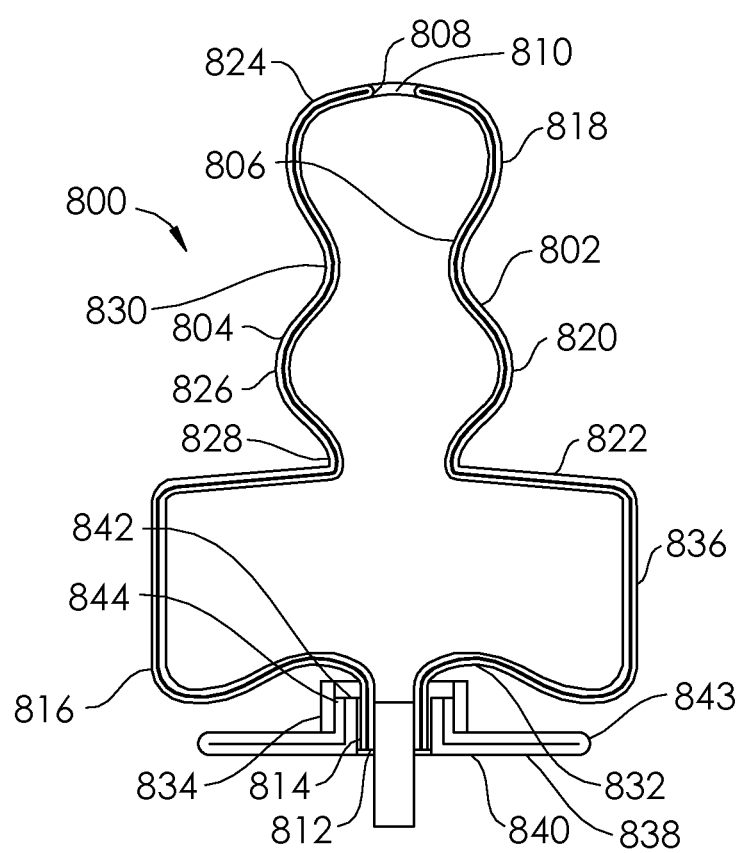
FIG. 28 is a sectional view of an alternative occlusion device, according to an embodiment of the present disclosure.

FIG. 28 illustrates an occlusion device 800 also comprising an inverted mesh tube 802 and having an outer layer 804, an inner layer 806, and an inversion fold 808, which creates a distal orifice 810, and serves as the transition between the outer layer 804 and the inner layer 806. The inverted mesh tube 802 has a first end 812 and a second end 814. The occlusion device 800 includes a proximal section 816, a distal section 818, and an intermediate section 820. The proximal section 816 has a substantially flattened portion 822, and the distal section 818 has a globular shape 824, configured to contact an aneurysm dome. The intermediate section 820 also has a globular shape 826. There is a waist 828 between the proximal section 816 and the intermediate section 820, and a circumferentially extending concavity 830 between the distal section 818 and the intermediate section 820. The proximal section 816 includes a proximal concavity 832 concavity, which is configured to clear a marker band 834. The proximal section 816 has a maximum diameter 836 configured to grip and internal wall of an aneurysm. The occlusion device 800 comprises a cover 838 configured to seat adjacent a neck of the aneurysm. In some embodiments, the cover 838 is circular, with substantially the same diameter at any transverse measurement around the perimeter. In other embodiments, the cover 838 is non-circular, and may comprise an ellipse, an oval, a polygon or other shapes. In the non-circular embodiments, the cover 838 comprises a minimum transverse dimension and a maximum transverse dimension. In the particular case of an ellipse or an oval shape, the cover 838 comprises a major diameter and a minor diameter. The minor diameter or minimum transverse dimension is configured to be larger than a maximum transverse dimension of an opening into the aneurysm (the neck portion). Thus, the cover 838 is configured to completely cover the neck portion, and thus to cause stagnation of blood within the aneurysm, leading to occlusion. The cover 838 is constructed from a mesh (braided) Nitinol (nickel-titanium alloy) tube 840 that is inverted on itself. The mesh tube 840 has a first end 842 and a second end 844. The second end 844 is folded back over the outer diameter of the first end 842. The mesh tube 840 is heat-formed such that cover 838 comprises an expanded portion 843 and the first end 842 and second end 844 comprise unexpanded (or partially expanded) portions. The cover 838 is fabricated as an inverted mesh tube 840 having a simple straight elongate configuration, and is subsequently formed into the shape shown in FIG. 28, and heat set into this shape. For example, the inverted mesh tube 840 may be constructed as a single layer mesh tube formed of at least some nickel-titanium alloy filaments, and then inverted on itself. The inverted mesh tube 840 may then be placed into a die or mold comprising one or more pieces, to hold it in the shape of the cover 838. Then, the cover 838 may be subjected to an elevated temperature and then cooled, to lock in the shape, resulting in a cover 838 having at least some superelastic properties.

The occlusion device 800 may comprise any of the materials and be made with any of the processes described in relation to the occlusion device 200, or any other of the occlusion devices described herein. The occlusion device 800 is configured to have flexing or articulating capabilities at the waist 828 and at the circumferentially extending concavity 830 which thus allow the proximal section 816, the distal section 818, and the intermediate section 820 to bend and conform to aneurysms of complex and irregular shapes. The maximum diameter 836 is configured to apply a radial force to the aneurysm wall to keep the occlusion device 800 in place, while the cover 838 facilitates thrombosis and closure of the aneurysm at the neck.

While the foregoing is directed to embodiments of the present disclosure, other and further embodiments may be devised without departing from the basic scope thereof. The filament diameter of the filaments comprising any of the mesh material (e.g., mesh tube including inverted mesh tubes) described herein may be between about 0.0004 inch and about 0.003 inch, or between about 0.0005 inch and about 0.002 inch, or between about 0.0006 inch and about 0.002 inch, or between about 0.0006 inch and about 0.0015 inch. The drawn filled tubes (DFT) may comprise between 0% and 100% of the total strands/filaments in any of the braided/mesh tubes. In some embodiments, the drawn filled tubes (DFT) comprise about 50% to about 100% of the total filaments of the cover and about 50% to about 100% of the total filaments of each of the doubled-over or looped tubular mesh. The radiopaque core of each of at least some of the drawn filled tubes has a cross-sectional area that is between about 10% and about 70% of the total cross-sectional area of the each of at least some of the drawn filled tubes, or between about 51% and about 70% of the total cross-ssectional area of the each of at least some of the drawn filled tubes. In some embodiments, NiTi #1-DFT® wire produced by Fort Wayne Metals Research Products Corp. (Fort Wayne, Ind. USA) may be utilized. The filaments may be braided with patterns having filament crossings that are in any one or more of the following ratios of filaments: 1×1, 1×2, 2×1, 2×2, 2×3, 3×2, 3×3, etc. (e.g., warp and weft). Any low, moderate, or high pick counts may be used, for example, between about 15 picks per inch and about 300 picks per inch, or between about 20 picks per inch and about 160 picks per inch. Any of the filaments or any of the portion of the occlusion devices may be coated with compounds that enhance endothelialization, thus improving the healing process when implanted within the aneurysm, and optimizing occlusion. The pusher and occlusion device configurations presented herein may also be used for in other types of implantable devices, such as stents, flow diversion devices, filters, and occlusion devices for structural heart defects.

Additional materials may be carried on the cover of the occlusion device, or any other proximal portion of the occlusion device, and configured to face opposite the aneurysm neck. In some embodiments, the material on the occlusion device may comprise a biological layer, configured to encourage growth. In some embodiments, the biological layer may comprise antibodies, in order to accelerate the formation of an endothelial layer, for example, by attracting endothelial progenitor cells (EPCs). In some embodiments, the biological layer may comprise a natural membrane or structure, such as a membrane, such as a membrane from an ear, or a cornea, or an ultra-thin piece of ligament, or even a piece of blood vessel wall. In some embodiments, the material on the occlusion device may comprise a polymer layer configured to act as a simulated arterial wall. In some embodiments, the polymer layer may comprise polytetrafluoroethylene, such as expanded polytetrafluoroethylene (ePTFE), such as that used in grafts. Occlusion devices as described herein may incorporate biological or polymeric layers, such as those described in co-pending U.S. patent application, Ser. No. 16/840,415, filed on Apr. 5, 2020, and entitled "Systems and Methods for Treating Aneurysms," which is hereby incorporated by reference in its entirety for all purposes.

The ranges disclosed herein also encompass any and all overlap, sub-ranges, and combinations thereof. Language such as "up to," "at least," "greater than," "less than,"

"between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An apparatus for treating an aneurysm in a blood vessel, comprising:
    an occlusion element having a distal end and a proximal end and configured to be releasably coupled to an elongate delivery shaft, the occlusion element comprising an inverted mesh tube having an outer layer and an inner layer, the outer layer transitioning to the inner layer at an inversion fold at the distal end of the occlusion element, the occlusion element configured to be delivered in a collapsed configuration through an inner lumen of a delivery catheter, the inner lumen having a proximal end and a distal end, the occlusion element further configured to expand to an expanded configuration when advanced out of the distal end of the inner lumen of the delivery catheter, wherein, in the expanded configuration, the outer layer of the inverted mesh tube has an expanded shape defined by:
    a proximally-facing surface;
    a frustoconical portion immediately adjacent to and extending distally of the proximally-facing surface, the frustoconical portion having a maximum transverse dimension B;
    a distally-facing surface immediately adjacent to a distal end of the frustoconical portion;
    a waist portion immediately adjacent to the distally-facing surface at a minimum transverse dimension thereof, the waist portion having a transverse dimension D; and
    a globular portion immediately adjacent to and extending distally from the waist portion to the inversion fold, the globular portion having a length L and a maximum transverse dimension CMAX, wherein dimension D is less than dimension B, wherein dimension D is less than dimension CMAX, and wherein, in the expanded configuration of the occlusion element, the waist portion is configured to be deformed by an externally applied force such that the globular portion is moved in relation to the distally-facing surface, wherein the globular portion has a first longitudinal axis and the frustoconical portion has second longitudinal axis, and wherein in the expanded configuration, the waist portion is configured to be deformed by an externally applied moment such that an angle between the first longitudinal axis and the second longitudinal axis is changed.

2. The apparatus of claim 1, wherein the waist portion, in a substantially undeformed state, has a longitudinal length of between about 0.05 mm and about 25 mm.

3. The apparatus of claim 1, wherein length L is between about 1 mm and about 25 mm.

4. The apparatus of claim 1, wherein the angle between the first longitudinal axis and the second longitudinal axis is changeable to a minimum angle of between about 90 degrees and about 135 degrees.

5. The apparatus of claim 1, wherein the waist portion comprises a bellows shape.

6. The apparatus of claim 1, wherein the waist portion comprises a circumferential concavity.

7. The apparatus of claim 1, wherein the frustoconical portion comprises a minimum transverse dimension A and wherein dimension A is between about 50% and about 100% of dimension B.

8. The apparatus of claim 7, wherein the frustoconical portion extends between dimension A and dimension B.

9. The apparatus of claim 7, wherein dimension A is between about 70% and about 90% of dimension B.

10. The apparatus of claim 7, wherein dimension $C_{MAX}$ is between about 50% and about 100% of diameter B.

11. The apparatus of claim 1, wherein the inner layer has an expanded shape which conforms with the expanded shape of the outer layer.

12. The apparatus of claim 1, wherein dimension B is about equal to dimension $C_{MAX}$.

13. The apparatus of claim 1, wherein dimension B is greater than dimension $C_{MAX}$.

14. The apparatus of claim 1, wherein the globular portion comprises a substantially hemispherical portion.

15. The apparatus of claim 1, wherein the proximally-facing surface comprises a substantially hemispherical portion.

16. The apparatus of claim 15, wherein globular portion comprises a substantially hemispherical portion.

17. The apparatus of claim 1, wherein the inversion fold is a circular shape surrounding an orifice that communicates with an internal volume of the occlusion element.

18. The apparatus of claim 1, wherein the globular portion has a generally cylindrical shape and a blunt distal end.

19. The apparatus of claim 1, wherein the globular portion has a length that is greater than dimension $C_{MAX}$.

20. The apparatus of claim 1, wherein the inverted mesh tube is formed from a plurality of filaments.

21. The apparatus of claim 20, wherein at least some filaments of the plurality of filaments, at the outer layer at the distal section, have an etched surface.

22. The apparatus of claim 20, wherein between about 50 percent and about 100 percent of the plurality of filaments comprise drawn filled tubes.

23. The apparatus of claim 22, wherein at least some of the drawn filled tubes comprises a radiopaque core having a cross-sectional area that is between about 51% and about 70% of the total cross-sectional area.

24. The apparatus of claim 1, further comprising a pusher having a proximal end and a distal end, wherein the occlusion element is configured to be releasably coupled to the distal end of the pusher at a releasable joint.

25. The apparatus of claim 24, further comprising a connection tube having a proximal end substantially flush with a proximal end of the occlusion element, a distal end extending within the occlusion element, and a lumen, wherein the distal end of the pusher extends through the lumen of the connection tube and comprises a plurality of radially extending protrusions located distal to the distal end of the connection tube, the plurality of radially extending protrusions forming a maximum transverse dimension that is greater than a maximum diameter of the lumen of the connection tube.

26. The apparatus of claim 25, further comprising an activator configured to modify the plurality of radially extending protrusions such that the distal end of the pusher can be fully removed from the lumen of the connection tube.

27. The apparatus of claim 26, wherein the activator is configured to cause an effect to the radially extending protrusions selected from the list consisting of: melting, detaching, unbending, breaking, ablating, and deforming.

28. The apparatus of claim 1, wherein the waist portion comprises a circumferential convexity.

29. The apparatus of claim 28, wherein the expanded shape of the outer layer further comprises a first circumferential concavity adjacent a first end of the circumferential convexity and a second circumferential concavity adjacent a second end of the circumferential convexity.

\* \* \* \* \*